United States Patent [19]

Kim et al.

[11] Patent Number: 5,691,204
[45] Date of Patent: Nov. 25, 1997

[54] COMPOSITIONS AND METHODS FOR THE RAPID ANALYSIS OF RETICULOCYTES

[75] Inventors: Young Ran Kim, Sunnyvale; Johanna Kantor, Palo Alto, both of Calif.

[73] Assignee: Abbott Laboratories, Abbott Park, Ill.

[21] Appl. No.: 426,408

[22] Filed: Apr. 21, 1995

[51] Int. Cl.$^6$ .................................................. G01N 33/48
[52] U.S. Cl. ........................... 436/63; 436/8; 436/10; 436/17; 436/18; 436/800; 435/6; 435/7.24; 435/7.25
[58] Field of Search .................... 436/8, 10, 17, 436/18, 63, 800; 435/6, 7.24, 7.25

[56] References Cited

U.S. PATENT DOCUMENTS

| | | | |
|---|---|---|---|
| 3,684,377 | 8/1972 | Adams et al. | 356/36 |
| 3,883,247 | 5/1975 | Adams | 356/39 |
| 4,336,029 | 6/1982 | Natale | 23/230 B |
| 4,544,546 | 10/1985 | Wang et al. | 424/7.1 |
| 4,707,451 | 11/1987 | Sage, Jr. | 436/63 |
| 4,751,181 | 6/1988 | Keene | 435/70 |
| 4,883,867 | 11/1989 | Lee et al. | 536/28 |
| 4,971,917 | 11/1990 | Kuroda | 436/63 |
| 4,978,624 | 12/1990 | Cremins et al. | 436/17 |
| 4,981,803 | 1/1991 | Kuroda | 436/63 |
| 4,985,176 | 1/1991 | Watanabe et al. | 252/521 |
| 5,004,804 | 4/1991 | Kuo et al. | 530/387 |
| 5,110,726 | 5/1992 | Ogden | 435/7.21 |
| 5,116,539 | 5/1992 | Hamaguchi et al. | 436/10 |
| 5,155,044 | 10/1992 | Ledis et al. | 436/17 |
| 5,175,109 | 12/1992 | Sakata et al. | 436/17 |
| 5,284,771 | 2/1994 | Fan et al. | 436/10 |
| 5,296,378 | 3/1994 | Sakata et al. | 436/63 |
| 5,308,772 | 5/1994 | Sakata et al. | 436/63 |
| 5,350,695 | 9/1994 | Colella et al. | 436/10 |
| 5,389,549 | 2/1995 | Hamaguchi et al. | 436/10 |
| 5,411,891 | 5/1995 | Fan et al. | 436/63 |
| 5,413,938 | 5/1995 | Tsujino et al. | 436/63 |
| 5,432,089 | 7/1995 | Ryan et al. | 436/10 |
| 5,434,081 | 7/1995 | Maekawa | 436/17 |
| 5,436,134 | 7/1995 | Haugland et al. | 435/34 |
| 5,438,003 | 8/1995 | Colella et al. | 436/63 |
| 5,451,525 | 9/1995 | Shenkin et al. | 436/63 |
| 5,496,734 | 3/1996 | Sakata | 436/63 |

FOREIGN PATENT DOCUMENTS 9424213   10/1994   WIPO .

OTHER PUBLICATIONS

Fujita "Detergents", Seita no Kagaku (1989), 40(4) 263–5. (Abstract).
Brecher, G., New Methylene Blue as a Reticulocyte Stain* Am. J. Clin. Pathol 19:895–896, 1949.
Heilmeyer, L., Ztschr. Klin Ned. 121:361–379, 1932.
National Committe for Clinical Laboratory Standards (NCCLS DOC.H44–P).

Primary Examiner—Jill Warden
Assistant Examiner—Sharidan Carrillo
Attorney, Agent, or Firm—Nicholas A. Poulos

[57] ABSTRACT

A method and reagent for the simultaneous or independent enumeration of reticulocytes in a whole blood sample, without the need to separately incubate the sample and reagent. The reagent contains a reticulocyte staining amount of an unsymmetrical cyanine dye, from about 40 mM to about 60 mM of a buffer selected from the group consisting of imidazole, Tris and Bis-Tris and a dye stabilizing amount of a non-ionic surfactant selected from the group consisting of N, N-bis[3-D-Glucon-amidopropyl] cholamide and a polyoxypropylene-polyoxyethylene block copolymer. The reagent has a pH from about 6.8 to about 7.2 and an osmolarity adjusted to about 280 to about 310 mOsm/l with a mono-, or di-, valent alkali salt selected from the group consisting of NaCl, KCl, LiCl, CaCl$_2$, MgCl$_2$ and ZnCl$_2$. The method utilizes the reagent in a no incubation process that also allows for the simultaneous determination of CBC as well as reticulocyte counts and maturity indices.

15 Claims, 15 Drawing Sheets

COMPOSITIONS AND METHODS FOR THE RAPID ANALYSIS OF RETICULOCYTES

The present invention relates to a method and stable aqueous reagent compositions for the rapid analysis of reticulocytes. More particularly the present invention relates to automatable methods and stable aqueous reagent compositions for the rapid analysis of reticulocytes utilizing light scatter and fluorescence flow cytometric techniques. The methods and stable aqueous reagent compositions enable the rapid analysis of reticulocytes, reportable by count and maturity, on high throughput multi-parameter hematology instruments. The method also permits the real-time analysis of reticulocytes and complete blood cell counts ("CBC"), including nucleated red cell counts ("NRBC"), without a separate incubation step.

BACKGROUND

Red blood cells ("RBC") normally enter the blood stream as reticulocytes. Erythropoiesis begins with the erythroblast and proceeds through about five generations of intermediate, nucleated cells in the bone marrow, and ending with the reticulocyte. The reticulocyte is an immature red blood cell which still contains reticular material (ribosomal and messenger RNA) even though at this stage of it's development the cell has expelled the nucleus.

Under anemic or hypoxic conditions this process may be shortened. Reticulocytes of an earlier stage than normal may enter the blood stream under these conditions. These early reticulocytes are recognized by the extra quantity of RNA they contain, as well as their larger size, lower content of hemoglobin, and by the greater length of time they persist as reticulocytes in the blood stream.

In the early 1930's, L. Heilmeyer (Ztschr. Klin. Ned. 121:361-379, 1932) differentiated reticulocytes into four age-groups according to the quantity of reticulum (vitally stainable substance contained within reticulocytes) they contain. Traditionally, Group I contains 30 or more reticulum, Group II contains 15-30, Group III contains 3-15, and Group IV contains 1-2 reticulum. The normal reticulocyte count is from about 0.5 to 2.5% of the RBC count for adults, and from about 2.0 to 6.0% of the RBC count for newborn infants. In terms of age groups, a normal adult will have the majority of reticulocytes in group IV, and none in group I.

The reticulocyte count is a measure of red cell production. It is useful, therefore, in the diagnosis and treatment of anemia. Historically, reticulocyte counts have been very closely associated with the etiology and classification of the anemias. The reticulocyte count is increased in hemolytic anemias, pyruvate kinase deficiency, sickle cell anemia, thalassemias, and decreased in megaloblastic anemia, aplastic anemia, general bone marrow dysfunction. Recently, the reticulocyte count has also been used to assess the toxic effects of chemotherapeutic agents on the marrow. Therefore, hematologists have unanimously promoted the reticulocyte count and reticulocyte maturity index as very valuable information.

The most commonly used method for counting reticulocytes is the manual microscopic procedure. Brilliant Cresol blue was predominantly used until New Methylene Blue ("NMB") was introduced in 1949 by G. Brecher (Am. J. Clin. Pathol. 19:895-896, 1949). The most recent National Committee for Clinical Laboratory Standards ("NCCLS") publication (NCCLS DOC. H44-P) endorses the NMB stain in which an equal volume of blood is mixed with NMB stain and incubated for about fifteen minutes to allow the RNA to precipitate. Blood smears are then made, and the stained reticulocytes are counted microscopically. A Miller ocular disc is inserted into an eyepiece. The area of the smaller square viewed within the eyepiece is 1/9 that of the larger square. The RBC are enumerated in the smaller square, while the reticulocytes are enumerated in the larger square. Twenty successive fields are counted and the % of reticulocytes is calculated by dividing total reticulocytes in large squares by total red blood cells in small squares after multiplying by 9. The draw back of the manual method is that it is labor intensive, imprecise, time-consuming and subjective.

Many attempts have been made to correct these shortcomings by means of flow cytometric technology. In the 1980's pyronin Y ("PY") and Acridin Orange ("AO") were used to stain and count reticulocytes on flow cytometers. Several semi-automated, flow cytometric methods are now available to enumerate reticulocytes from a whole blood sample. In each of the existing methods, a diluent containing an organic cationic dye, such as Auramine O ("AuO"), or Thiazole Orange ("TO") is used to stain the RNA within the reticulocytes. During the incubation period, the dye slowly penetrates the cell membrane and binds to the RNA within each reticulocyte. The amount of signal generated by the stained reticulocytes as the sample passes through the detection zone is roughly proportional to the RNA content within each reticulocyte. A flow cytometer equipped with the proper excitation light source and emission detection system can, therefore, be used to determine the percentage of reticulocytes in a whole blood sample.

However, there are many sources of problems complicating the automation of reticulocyte methodologies, especially when the instrument is a multi-parameter hematology system. The most important of which is the necessity to prepare a stained sample "off-line". This sample preparation step requires a lengthy incubation period of several minutes or longer before the dye has penetrated the cell to sufficiently stain the reticulocyte's RNA to enable the sample to be processed through a flow cytometer. In addition, the majority of the dyes currently in use to stain RNA in the reticulocytes are not stable in aqueous solutions and bind not only to RNA and DNA but can also bind to the instrument's plastic tubing, glass surfaces, including the flow cell. This requires the long and arduous task of cleaning the complete system after running the test.

U.S. Pat. No. 3,684,377 to Kaminsky, et al., U.S. Pat. No. 3,883,247 to Adams and U.S. Pat. No. 4,336,029 to Natale, all disclose the use of AO for staining reticulocytes. Although AO has excellent properties for staining reticulocytes (it binds to RNA and generates red fluorescence), it also binds to plasma and generates high background sample stream fluorescence, making it very difficult to obtain a good signal to noise ("S/N") ratio. Even more problematical, using AO on a flow cytometer is AO'S propensity to bind to plastic tubing and flow cell surfaces, adding to the detection problems. In addition, the AO methods require 5 to 7 minutes to incubate which is much too long a time period to be incorporated onto the high throughput multi-channel hematology analyzers of today.

U.S. Pat. No. 4,707,451 to Sage, Jr. discloses a reagent composition comprised of thioflavin T or chrysaniline. The dye uptake by reticulocytes takes about 7 minutes in this method and the background fluorescence is too high to obtain a good S/N ratio in Group IV reticulocyte detection.

U.S. Pat. No. 4,883,867 to Lee et al. discloses a dye for staining RNA and DNA. TO is their preferred dye for reticulocyte analysis and the method requires a minimum incubation time of 30 minutes. Although TO has a high nucleic acid binding affinity and quantum yield, the rate of membrane permeation by TO is very slow (30 minutes) and thus, is unsuitable for use on a high throughput multi-parameter clinical hematology instrument.

U.S. Pat. No. 4,971,917 to Kuroda teaches a reagent composition which contains AuO and a carbonate salt to reduce the non-specific staining of the mature erythrocytes. U.S. Pat. No. 4,985,176 discloses another reticulocyte staining reagent for flow cytometric use in which AuO is included as a preferred dye and the sample incubation time for staining is anywhere between 30 seconds to 20 minutes. The disadvantages of using AuO on a flow cytometer is that the dye, like AO, has an affinity not only to DNA and RNA but also to various types of plastic and glass surfaces, making it extremely difficult to incorporate the methods into a multi-parameter hematology instrument. TOA Medical Electronics Co., Ltd. has managed to incorporated an AuO method onto it's Sysmex® R-1000 and R-3000 automated, stand-alone reticulocyte analyzers, but has been unable to incorporate the method onto their multi-parameter hematology instruments such as the NE8000 or SE9000 instruments.

U.S. Pat. No. 5,284,771 to Colella et al. discloses a method and a reagent composition which comprises treating a whole blood sample with a single reagent solution containing a cationic dye (Oxazine® 750) to stain RNA in reticulocytes and a zwitterionic sphering agent to eliminate the orientational noise of the flat red blood cell when the stained subjected to flow cytometric light measurement system.

Recently, Miles Inc. has incorporated the above method on their latest H*3® hematology instrument. This instrument is equipped with a helium/neon ("HeNe") electro-optical detection system and Oxazine® 750 nucleic acid dye is used to stain reticulocytes while a zwitterionic surfactant is used to sphere the red blood cells and reticulocytes in preparation for volumetric measurements. The H*3® reticulocyte method is only a semi-automated method which requires manual mixing of the blood with the reticulocyte reagent followed by a 15 minute off-line incubation. The sensitivity of the method in detecting Group IV reticulocytes is poor.

Coulter Corporation has also incorporated a semi-automated reticulocyte method on their STKS® and Maxim® hematology analyzers. Coulter calls their technology: VCS (Volume, Conductivity and Scatter). In practicing VCS, a blood sample is first mixed with Coulter's retic dye (which contains NMB). The mixture is then incubated at room temperature for 5 minutes. Then, a small volume of the stained blood sample is diluted with a clearing solution which contains sulfuric acid. The accuracy of the method suffers greatly from poor sensitivity and a poor resolution of the red blood cells. This is due to reticulocyte stroma (lysed by the clearing solution), other cellular debris and platelets creating noise, making it very difficult to differentiate the proper signals. Only clumped platelets will generate signals that are larger and which, therefore, will not interfere with the signals generated by RBC and reticulocyte stroma.

U.S. Pat. No. 4,981,803 to Kuroda discloses a reagent containing AuO for reticulocyte counting by flow cytometric methods which comprises two solutions, a stock solution for staining, in which a dye (AuO) is dissolved in a non-aqueous solvent, and a buffer solution which satisfies the optimum staining conditions for RNA in reticulocytes. Kuroda claims that by combining these two solutions immediately before staining, a stable final staining solution for reticulocyte counting can always be obtained. The problems of this method are many. Most importantly, the group of non-aqueous solvents that they selected (ethylene glycol, triethylene glycol, diethylene glycol) have a high, refractive index. Such indices of refraction make them unsuitable for use on a multi-parameter hematology analyzer. This is due to the aqueous sheath solution which is necessary (such as phosphate buffered saline) and which has a refractive index of about 1,334. As described in the Kuroda patent, other solvents, such as methanol, ethanol or propanol (which have refractive index close to saline sheath) are highly volatile and thus, are also unsuitable. Additionally, it is technically very difficult to mix such small amounts of stock solutions with large volumes of aqueous buffer on-line, as is required by this methodology, to provide a stable reticulocyte reagent.

Therefore, a long felt need has existed for a rapid and accurate method for reticulocyte analysis which can be incorporated on a flow cytometer or a high throughput multi-parameter hematology analyzer while utilizing a reagent that is stable in an aqueous environment.

SUMMARY OF THE INVENTION

A method for the simultaneous enumeration of CBCs and reticulocytes in a whole blood sample, without the need for a separate incubation step for the reticulocyte enumeration, is provided.

One embodiment provides for an aqueous, nucleic acid staining reagent which comprises a reticulocyte staining amount of an unsymmetrical cyanine dye, from about 20 mM to about 60 mM of a buffer solution selected from the group consisting of imidazole, Hepes, Bis-Tris and Tris buffers, and a dye stabilizing amount of a non-ionic surfactant selected from the group consisting of N,N-bis[3-D-Glucon-amidopropyl]cholamide, n-Dodecyl-D-Maltoside, a polyoxypropylene-polyoxyethylene block copolymer, n-Tetradecyl-D-Maltoside, Decanoyl-N-methyl-glucamide, n-Dodecyl-D-glucopyranoside and n-Decyl-D-glucopyranoside. The reagent has a pH from about 6.0 to about 8.0 and an osmolarity adjusted to about 230 to about 340 mOsm/l with mono-, or di-, valent alkali salts which do not interfere with the cyanine dye or precipitate in the aqueous reagent solution.

In another embodiment a method of enumerating reticulocytes is provided. First an aliquot of a whole blood sample is mixed with the aqueous, nucleic acid staining reagent. This sample/reagent aliquot is then transported to an optical flow cell for analysis without separately incubating the aliquot. While passing the cells through an illuminated optical flow cell, essentially one cell at a time, the light scatter and the fluorescent characteristics are detected and the enumeration of reticulocytes in the sample is determined therefrom.

A further embodiment provides an aqueous, nucleic acid staining reagent which comprises from about 0.1 µg/ml to about 0.3 µg/ml of a dye selected from the group consisting of 2-butyl-4-[2,3-dihydro-3-methyl-(benzo-1,3-thiazol-2-yl)-methylidene]-1-phenylquinolinium iodide, 2-diethylamino-4-[2,3-dihydro-3-methyl-(benzo-1,3-thiazol-2-yl)-methylidene]- 1-phenylquinolinium iodide, 2-methylthio-4-[2,3-dihydro-3-methyl-(benzo-1,3-thiazol-2-yl)-methylidene]-1-phenylquinolinium iodide, and 4-[2,3-dihydro-3-methyl-(benzo-1,3-thiazol-2-yl)-methylidene]-1-phenylquinolinium tosylate (all obtainable from Molecular Probes, Eugene, Ore.), from about 40 mM to about 60 mM of imidazole buffer, and a dye stabilizing amount of a non-ionic surfactant selected from the group consisting of N,N-bis[3-D-Glucon-amidopropyl]cholamide and a polyoxypropylene-polyoxyethylene block copolymer wherein the reagent has a pH from about 6.8 to about 7.2 and an osmolarity adjusted to about 280 to about 310 mOsm/l with a mono-, or di-, valent alkali salt selected from the group consisting of NaCl, KCl, LiCl, $CaCl_2$, $MgCl_2$ and $ZnCl_2$.

In yet another embodiment a method for the simultaneous enumeration of reticulocytes and a complete blood cell count is provided. While an aliquot of a whole blood sample is being analyzed for a CBC determination a second aliquot of the sample is being mixed with the aqueous, nucleic acid staining reagent and the reticulocyte component of the sample is analyzed as described above.

BRIEF DESCRIPTION OF THE DRAWINGS

FIG. 1b is an FL1 histogram of the gated red blood cell ("RBC") population of FIG. 1a.

FIG. 3b is the FL1 histogram of the gated RBC population the blood sample of FIG. 3a.

FIG. 15b is the FL1 histogram of the gated red cell population of FIG. 15a.

DETAILED DESCRIPTION OF THE INVENTION

Figure 1A:
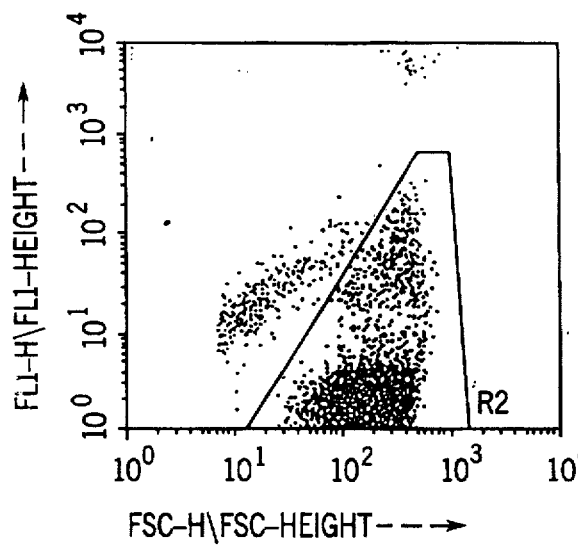
FIG. 1a is a two dimensional FAtScan® display (cytogram) of forward Scatter ("FSC") vs green fluorescence ("FL1") signals of a clinical sample with 5.63% reticulocytes.

Embodiments of the present invention comprise methods and stable aqueous reagent systems for the rapid and accurate analysis of a blood sample for reticulocytes by utilizing flow cytometric methodologies. Generally, these embodiments relate to the rapid and simultaneous analysis of reticulocytes and complete blood cell counts ("CBC"), including nucleated red blood cells ("NRBC"). Embodiments of the present invention can comprise the use of an analytical instrument and a method for analyzing blood. Generally, one such analytical instrument includes an automated impedance analyzer. In one such automated instrument an automated light scatter analyzer is integrated with the automated impedance analyzer, and an automated fluorescence analyzer is integrated with the automated light scatter analyzer.

For the sake of this disclosure, an automated analyzer is distinguished in that an operator does not need to intervene in analysis of the sample, viz. after the operator presents the sample to the automated analyzer, no further operator intervention is required. Additionally, a hematology analyzer quantifies and classifies cells in substantially absolute terms. Such an analyzer uses at least one of electrical impedance and optical scattering properties of the cells to classify cells by size and shape.

Implementations of the invention can generally utilize an automated hematology analyzer with a controller which monitors and controls the various analyzers, collects data from the analyzers and reports a result. Illustrating by example, integration of the analyzers with a controller allows an operator to input data about a whole blood sample into the controller. The operator selects a bank of tests to be performed on the whole blood sample with the aid of the controller. The operator presents the whole blood sample to the integrated analyzers at a centralized sample processing area. The controller activates the analyzers, allowing the analyzers to automatedly perform analyses on the whole blood sample under the direction of the controller. The controller utilizes data obtained from the analyzers to formulate a result. The controller reports the result to the operator. It is to be noted that no operator action is needed after the whole blood sample is presented to the integrated analyzers. Because the whole blood sample preparation is entirely automated, in a preferred embodiment, conventional hematology tests are done first with the incubated sample tests to follow. Because the analyzers are integrated with the controller, the controller obtains data from both the hematology analyzer and the flow cytometry analyzer. Thus, the controller is able to report a combined patient blood analysis to the operator.

While specific embodiments of the invention will be discussed in detail to clarify understanding, it is to be remembered that other embodiments are also possible. Any desirable combination of elements of the described embodiments is also possible.

In one aspect of the invention a stable, aqueous reagent composition is provided. This reagent comprises: an unsymmetrical cyanine dye capable of staining reticulocytes, from about 20 mH to about 50 mH of a buffer selected from the group consisting of Imidazole buffer, 4-(2-Hydroxyethyl)-1-perperazineethane-sulfonic acid ("Hepes") buffer, Bis (2-Hydroxyethyl)-1-piperazineethane-sulfonic acid ("Bis-Tris") buffer and Tris Hydroxymethyl Aminomethane ("Tris") buffer; a pH from about 6.0 to about 8.0; an osmolarity adjusted to about 230 to about 340 mOsm/L with a mono, or di, valent alkali salt; and a non-ionic surfactant (from about 5 mg/dl to about 1.0 g/dl depending on the surfactant) which facilitates the membrane permeation and stabilizes the cyanine dyes in an aqueous isotonic solution. Preferably the dyes are cyclic substituted and exhibit enhanced fluorescence upon binding with DNA or RNA. Even more preferably, the reagent comprises from about 0.1 µg/ml to about 0.3 µg/ml of a cyclic substituted, unsymmetrical cyanine dye.

Another aspect involves methods for the rapid and continuous detection and enumeration of reticulocytes and CBC differentials, utilizing the present inventive reagent system. Such methods are distinct due to the particular absence of the need to provide for a separate incubation step. The incubation minimal period required, from about 10 to 60 seconds is all that is necessary.

One such embodiment is a method of enumerating reticulocytes from a whole blood sample while simultaneously differentiating a separate aliquot of the sample to obtain a complete blood cell ("CBC") analysis. This method comprises, directing one or more aliquots of the sample to various positions within an automated analyzer for analysis and differentiation, while a reticulocyte aliquot of the sample is combined with a staining reagent. This reagent comprises, a reticulocyte staining amount of an unsymmetrical cyanine dye, from about 20 mM to about 60 mM of a buffer solution, selected from the group consisting of imidazole, Hepes, Bis-Tris and Tris buffers, and a dye stabilizing amount of a non-ionic surfactant selected from the group consisting of N,N-bis[3-D-Glucon-amidopropyl] cholamide, n-Dodecyl-D-Maltoside, a polyoxypropylene-polyoxyethylene block copolymer, n-Tetradecyl-D-Maltoside, Decanoyl-N-methylglucamide, n-Dodecyl-D-glucopyranoside and n-Decyl-D-glucopyranoside, wherein said reagent has a DH from about 6.0 to about 8.0 and an osmolarity adjusted to about 230 to about 340 mOsm/l with a mono-, or di-, valent alkali salt which does not interfere with the cyanine dye or precipitate in the aqueous reagent solution such as NaCl, KCl, LiCl, $CaCl_2$, $MgCl_2$ and $ZnCl_2$. The combined reagent/reticulocyte aliquot is then directed to an optical sensing zone of an automated analyzer. Thereafter the reagent/reticulocyte aliquot is passed through an illuminated sensing zone essentially one cell at a time to cause fluorescence and scattered light events. These events are detected and the number of reticulocytes present in said sample are determined therefrom.

The unsymmetrical dyes usable with the reagent system of the present invention generally have the following characteristics:

1. Absorption Maxima: 488±20 nm
2. High nucleic acid binding affinity
3. High quantum yield: $\geq 0.1$
4. Molar Extinction Coefficient: $\geq 10,000$
5. Fluorescence Enhancement upon binding to RNA or DNA: $\geq 20$
6. Membrane Permeation Rate: <2 minutes Typically, the dyes utilized in this inventive aqueous reagent and reticulocyte enumerating methods are highly unstable in aqueous environments. The stability data for several dyes tested in this class are shown in FIGS. 10 through 14.

One embodiment of the present reagent system comprises from about 0.05 µg/ml to about 0.5 µg/ml of 2-butyl-4-[2, 3-dihydro-3-methyl-(benzo-1,3-thiazol-2-yl)-methylidene]-1-phenylquinolinium iodide, a proprietary dye sold by Molecular Probes, Inc. (Eugene, Ore.), from about 20 mM to about 50 mM Imidazole buffer, and from about 5 mg/dl to about 20 mg/dl of N,N-bis[3-D-Glucon-amidopropyl] cholamide ("BIGCHAP"), from about 0.02% to about 0.05 5% Proclin® 300 (5-chloro-2-methyl-4-isothiazoline-3-one+2-methyl-4-isothiazoline-3-one). The pH is adjusted to from about 6.8 to about 7.2 with 1N HCl and the Osmolarity adjusted with NaCl from about 270 to about 310 mOsm/L.

A main ingredient of the reagent system is the dye. One such class of dyes are unsymmetrical cyanine dyes such as those disclosed in WO94/24213, "CYCLIC-SUBSTITUTED UNSYMMETRIC DYES", and herein incorporated by reference. Additionally, the dyes utilized in this invention exhibit enhanced fluorescence upon binding with DNA or RNA. Such useful dyes must also have high binding affinity to RNA and DNA and a high quantum yield. It is anticipated that a variety of unsymmetrical cyanine dyes which exhibit the characteristics described and claimed herein can be used. Some of the examples of such dyes include, but are not limited to 2-butyl-4-[2,3-dihydro-3-methyl-(benzo-1,3-thiazol-2-yl)-methylidene]-1- phenylquinolinium iodide, 2-diethylamino-4-[2,3-dihydro-3-methyl-(benzo-1,3-thiazol-2-yl)-methylidene]-1-phenylquinolinium iodide, and 2-methylthio-4-[2,3-dihydro-3-methyl-(benzo-1,3-thiazol-2-yl)-methylidene]-1-phenylquinolinium iodide, also obtained from Molecular Probes, Inc. (Eugene, Ore.) ("MPI"). Other unsymmetrical cyanine dyes such as 4-[2,3-dihydro-3-methyl-(benzo-1,3-thiazol-2-yl)-methylidene]-1-phenylquinolinium tosylate, also sourced from MPI, are also useful in practicing the present invention. 4-[2,3-dihydro-3-methyl-(benzo-1,3-thiazol-2-yl)-methylidene]-1-phenylquinolinium tosylate is believed to be a neutral, unsymmetrical cyanine dye comprising a substituted benzazolium ring system linked to a methine bridge to a pyridinic or quinoline ring system.

A further ingredient of the reagent system is a buffer whose pKa is from about 6.0 to about 8.0 and is capable of maintaining the required (for staining RNA or DNA) concentration of the cyanine dye in an aqueous solution in an extended period of time. Such buffers should not react with the cyanine dyes or the non-ionic surfactants used in the practice of this invention to stabilize the dye. Exemplary buffers include Imidazole, Hepes, Bis-Tris, and Tris.

Another ingredient of the reagent system is a non-ionic surfactant. Depending upon the surfactant, or combination of non-ionic surfactants, that are use, the concentration should be from about 5 mg/dl to about 1 g/dl. The surfactant(s appear to enhance the rate of the cyanine dye permeation through the cell membrane (within 30 seconds). In addition, the solubility and the stability of the cyanine dyes in an isotonic aqueous solution are enhanced by the surfactant. Such surfactant(s) should not, however, precipitate or react with the cyanine dyes or lyse RBCs, even at the low concentrations. Examples of such surfactants are, but are not limited to, BIGCHAP, n-Dodecyl-D-Maltoside, Polyoxypropylene-polyoxyethylene block copolymer ("Pluronic® F127"), n-Tetradecyl-D-Maltoside, Decanoyl-N-methyl-glucamide, n-Dodecyl-D-glucopyranoside and n-Decyl-D-glucopyranoside.

Yet another ingredient of the reagent system is a mono-, or di-, valent alkali salt to adjust the osmolarity of the reagent from about 230 mOsm/L to about 340 mOsm/L to prevent the lysis of red cells, including the reticulocytes, or the white cells. Such salts should not react with the either the cyanine dyes or precipitate in solution. Examples of such salts include NaCl, KCl, LiCl, $CaCl_2$, $MgCl_2$, $ZnCl_2$ and others.

An optional ingredient, is a preservative to prevent microbial growth in the reagent. Such a preservative should not change the light scattering or fluorescent emission properties of the cells, or stained cells. Examples of such preservatives include Proclin® 300, Proclin® 150 (5-chloro-2-methyl-4-isothiazolin-3-one (1.05%–1.25%) and 2-methyl-4-isothiazolin-3-one (0.25%–0.45%), sodium azide and others.

Utilizing the above described reagent system the rapid analysis of reticulocytes on a flow cytometer, or other automated hematology analyzer, is possible. In one embodiment, 5 μl of a whole blood sample is mixed with 1.0 ml of the reagent system disclosed and claimed herein, and the sample/reagent mixture is run on a commercially available flow cytometer within 30 to 60 seconds of mixing, and as little as ten (10) seconds. FIGS. 1a through 1d show the results of such a method using a normal blood sample prepared as described in Example 1.

A further embodiment of the present invention allows for the rapid and quantitative analysis of reticulocytes on an automated high throughput multi-parameter hematology analyzer. U.S. patent application Ser. No. 08/283,379, entitled "METHOD AND APPARATUS FOR PERFORMING AUTOMATED ANALYSIS", filed on Aug. 1, 1994, and incorporated herein by reference, discloses an automated hematology analyzer which utilizes light scatter signals axial light loss ("ALL") and intermediate angle scatter ("IAS"), among others, as well as detecting various fluorescent signals to enable the instrument to automatically differentiate cells and subclasses of cells from a whole blood sample.

Generally, however, a method for practicing the present invention comprises the mixing of a whole blood sample with a reagent to stain the RNA of any reticulocytes present, flowing the mixture, essentially one cell at a time, through an illuminated optical flow cell, detecting the light scattered and fluorescence emitted therefrom and determining the amount of reticulocytes present in the sample without subjecting the sample/reagent mixture to a separate incubation step or period. One reagent of this invention comprises from about 0.1 μg/ml to about 0.3 μg/ml of an unsymmetrical cyanine dye; from about 20 mM to about 60 mM of a buffer selected from the group consisting of Imidazole, Hepes, Bis-Tris, and Tris buffers; from about 5 mg/dl to about 1.0 g/dl of a non-ionic surfactant, depending on the surfactant or combination of surfactants, and the reagent has a pH from about 6.0 to about 8.0; and an osmolarity adjusted to about 230 to about 340 mOsm/L with a mono-, or di-, valent alkali salt.

In order to analyze a whole blood sample for the percentage as well as the absolute counts of reticulocytes on the multi-parameter hematology analyzer described above, about 18.75 μl of a whole blood sample is deposited by means of a sample aspiration probe into an RBC cup which contains about 7856 μl of a diluent/sheath solution (an isotonic saline) and the fluids are mixed. The diluted sample is then transported to a sheathed impedance aperture to electronically determine the absolute RBC counts of the sample (see details of instrument calibration for RBC analysis in U.S. patent application Ser. No. 08/283,379, entitled "METHOD AND APPARATUS FOR PERFORMING AUTOMATED ANALYSIS", filed on Aug. 1, 1994, and incorporated herein by reference). In the mean time, about 200 μl of the diluted sample is transferred into another receptacle ("reticulocyte receiving cup"), which contains 600μl of the reagent of the present invention, where it is mixed. The prepared (mixed) sample is then transported to the sheathed optical flow cell for detection. The measurement process begins as the cell stream passes through the flow cell essentially one cell at a time, in a laminar flowing sample stream surrounded by a diluent/sheath solution. The volume is illuminated by a beam of light and is bounded in the two dimensions normal to the flow axis by the hydrodynamically focused cell stream, and in the dimension parallel to the flow axis by the vertical beam waist of the laser beam which is about 17 microns. When doing this test, the sample flow rate is about 2.0 μl per second, and the corresponding illuminated sensing volume of the RBC and reticulocyte sample stream approximates an elliptical cylinder with dimension of about 80×5×17 microns. The 17 micron dimension is measured along the axis of the cylinder.

Figure 4A:
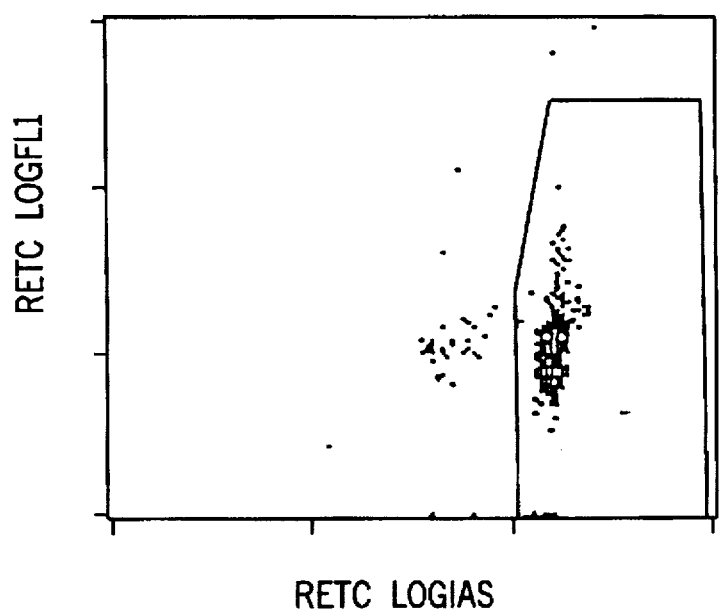
FIG. 4a is an Abbott Laboratories hematology analyzer cytogram of a sample of normal blood showing the four decade log Intermediate Angle Light Scatter ("IAS") vs the four decade log FL1.

At this point, and as shown in the two dimensional feature space of IAS and FL1 of the cytogram of FIG. 4a, the presence of a cell is detected by an intermediate angle scatter photo-diode which detects light in a 3° to 10° cone, and a photomultiplier tube ("PMT") which detects green fluorescence, FL1. When cells pass through the aforementioned illuminated volume, pulses are generated and measured by these detectors. The amplitudes of these pulses are then filtered, amplified, digitized, and stored in list mode in the corresponding two dimensional feature space of IAS and FL1. The cells are counted for 8 seconds. At the flow rate and the dilution ratio described above, with a normal subject RBC counts of 5 millions per microliter of blood volume, the resulting event count rate would be 5950 per second. Algorithms are then applied to the list mode data of the aforementioned feature space of IAS and FL1 and the following parameters are measured within 20 seconds of computational time:

1. RBC gate: WBCs and platelets are excluded by gating the RBC population, including reticulocytes, but excluding WBCs and platelets.

2. The percent of reticulocytes: The gated RBC population is re-analyzed according to the size of their FL1 signals. A log fit is applied to the FL1 histogram to define the region which belongs to mature RBCs, and the cells whose FL1 signals fall above the region are labeled as reticulocytes. Reticulocyte % is computed by dividing the counts of reticulocytes by the total RBC counts.

3. The absolute reticulocyte counts: Obtained by multiplying the percent of reticulocytes by absolute RBC counts of the sample from the CBC mode.

4. Reticulocyte Maturity Index ("RMI"): RMI is expressed as the percent of reticulocytes whose FL1 signals are more than one (1) standard deviation ("S.D.") above the mean fluorescence of a normal reticulocyte population.

Such a description is merely for convenience and by no means is the expression of RMI of the present invention limited to only the algorithms discussed herein.

The following examples set forth reagent compositions and methods incorporating the same for the rapid analysis of reticulocytes using light-scatter and fluorescence flow cytometric techniques. It will be understood that the following examples are for illustrative purposes only and are not intended to limit the scope of this invention in any manner.

EXAMPLE 1

Figure 1B:
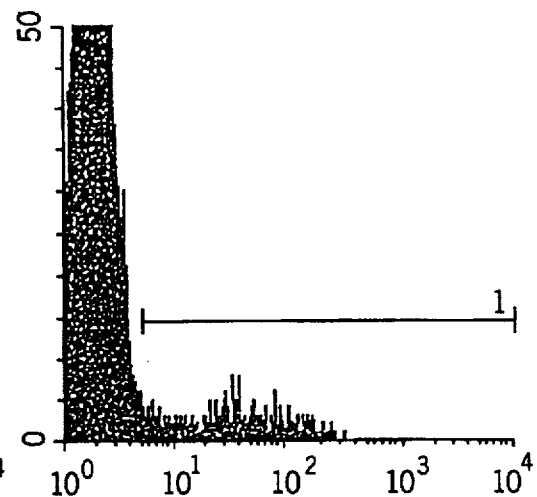
Figure 1C:
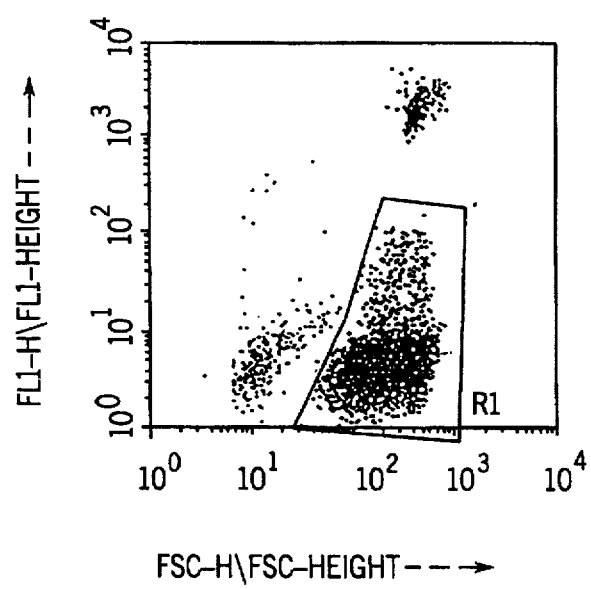
FIG. 1c is a FACScan® cytogram of FSC vs FL1 signals of a clinical sample with 2.63% reticulocytes and elevated white blood cell ("WBC") population.
Figure 1D:
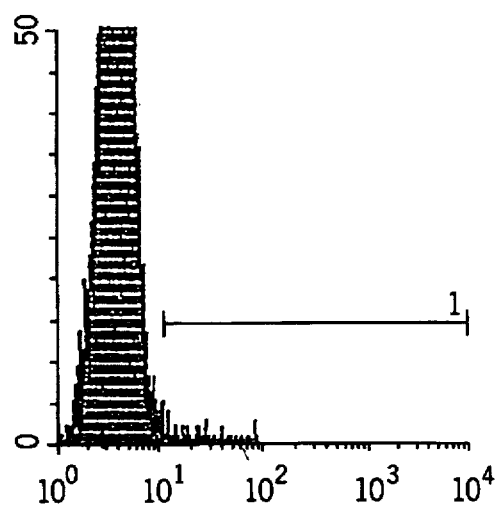
FIG. 1d is an FL1 histogram of the gated RBC population of FIG. 1c.

Five (5) microliters of a clinical sample was mixed with 1.0 ml of the reagent comprising 50 mM imidazole buffer, DH adjusted with 1N HCl to 7.0+0.1, 6.4 g/L NaCl, 0.1 micrograms per ml of 2-diethylamino-4-[2,3-dihyro-3-methyl-(benzo-1,3-thiazol-2-yl)-methylidene]-1-phenylquinolinium iodide (Molecular Probes, Inc., Eugene, Ore.), 0.2% Pluronic® F127, and 0.03% Proclin® 300. The sample/reagent mixture is then run within 30–60 seconds on a FAGScan® flow cytometer (Becton Dickinson & Co.) to determine the rate of membrane-permeation by the dye in the reagent composition. FIG. 1a is a two dimensional display of forward Scatter (FSC) vs green fluorescence (FL1) signals; FIG. 1b is the FL1 histogram of the gated red cell population revealing the stained reticulocyte population to the right of the mature RBC population. FIGS. 1c and 1d show the results of a second clinical sample displayed a similar manner as FIGS. 1a and 1b, respectively.

EXAMPLE 2

Figure 2A:
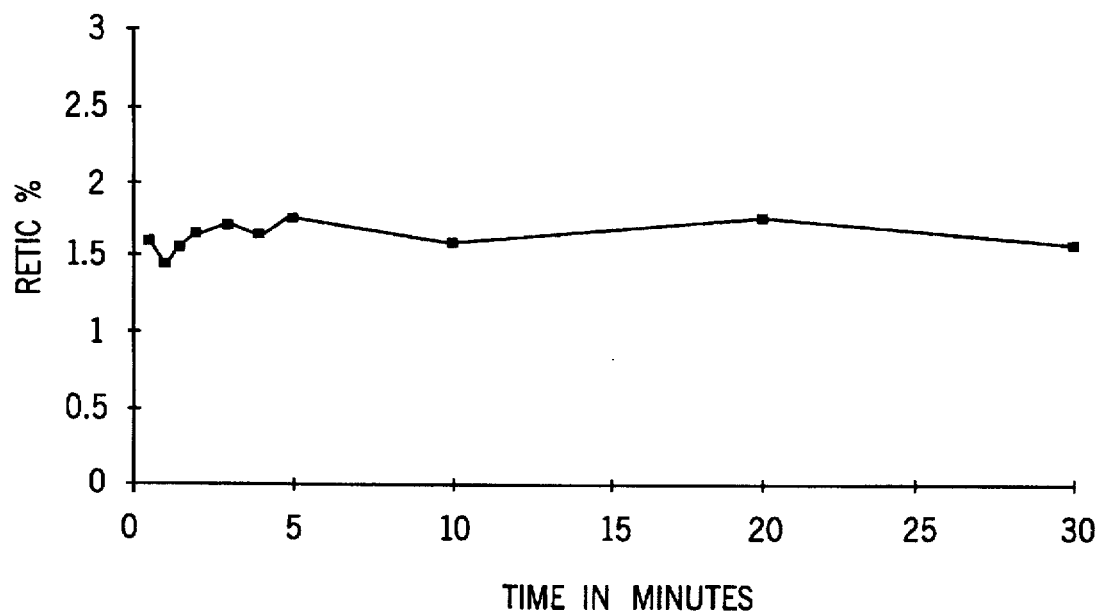
FIGS. 2a and 2b are graphical depictions of the results of a time study performed on a FACScan® instrument.
Figure 2B:
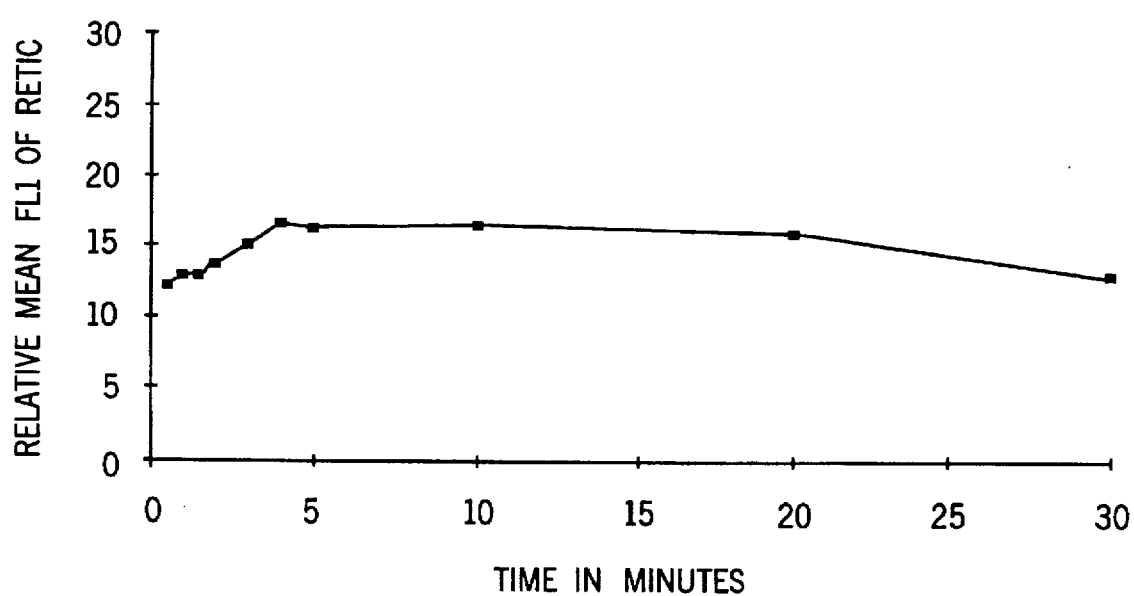

FIG. 2a is a time study performed on the FACScan® flow cytometer expressed as reticulocyte % over an extended time period (from 30 seconds to 30 minutes) and FIG. 2b is expressed as reticulocyte mean FL1. As can be seen in the Figures, the % of reticulocyte reaches the steady state within 30 seconds and the staining intensity reaches about 80% of the peak within 30 seconds. Such rapid staining by means of the present invention enables the incorporation of the method and reagents disclosed herein, onto automated hematology analyzers, as well as flow cytometers, without the need for separate incubation equipment, or methods.

EXAMPLE 3

Figure 3A:
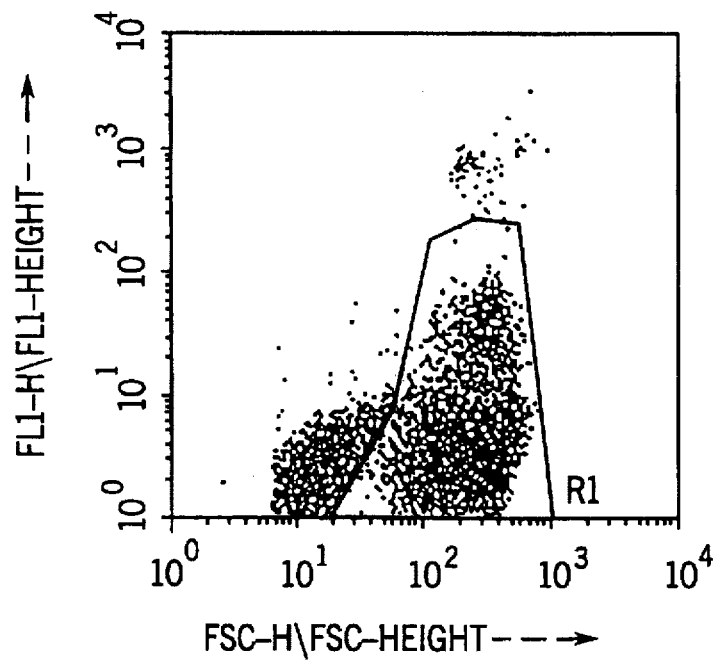
FIG. 3a is a FACScan® cytogram of FSC vs FL1 signals of a clinical sample with elevated reticulocytes
Figure 3B:
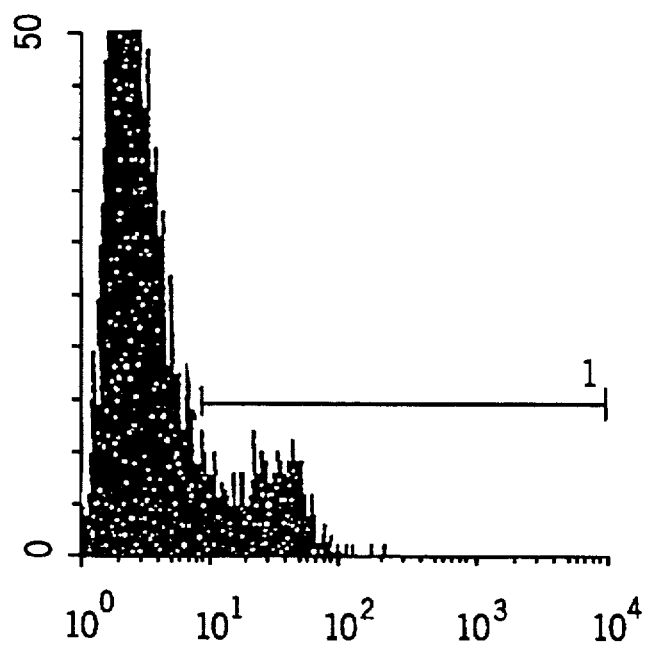

Five (5) microliters of a clinical samples with about 15% reticulocytes were mixed with 1.0 ml of the reagent of the present invention comprised of 50 mM imidazole buffer, pH adjusted with 1N HCl to 7.0+0.1, 6.4 g/L NaCl, 0.2 micrograms/ml of 2-butyl-4-[2,3-dihydro-3-methyl-(benzo-1,3-thiazol-2-yl)-methylidene]-1-phenylquinolinium iodide (Molecular Probes, Inc., Eugene, Ore.), 0.2% Pluronic® F127, and 0.03% Proclin® 300. The sample/reagent mixtures were then run on a FAGScan® flow cytometer within 30 seconds to determine the % of reticulocytes in the samples. FIG. 3a is a two dimensional display of FSC vs FL1 signals and FIG. 3b is the FL1 histogram of the gated red cell population. As the data show, WBCs and platelets are well separated from the RBC and reticulocyte population, the FL1 intensity of the stained reticulocytes is such that defining the region of reticulocytes in the FL1 histogram of red cells is easy for quantitative analysis of reticulocyte concentration in a blood sample.

EXAMPLE 4

Figure 4B:
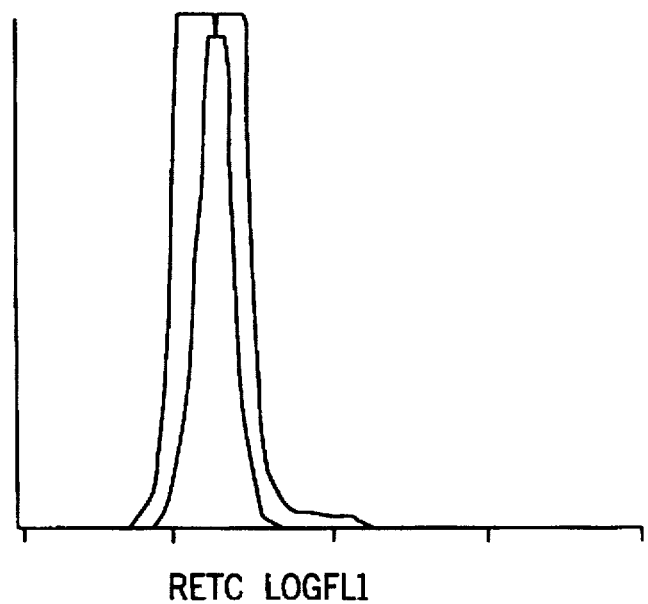
FIG. 4b is a FL1 histogram of the gated RBC population and reticulocyte population from FIG. 4a. The 1× scale display of the histogram shows the RBC Peak and the 5× scale displays of the histogram exhibits the reticulocyte population.

For this example, an automated, high-throughput multi-parameter hematology analyzer (U.S. patent application Ser. No. 08/283,379, entitled "METHOD AND APPARATUS FOR PERFORMING AUTOMATED ANALYSIS", filed on Aug. 1, 1994) was used. 18.75 μl of an EDTA-anti coagulated whole blood sample from a normal subject was deposited by means of a sample aspiration probe into the RBC cup which contains about 7856 μl of a diluent/sheath solution (an isotonic phosphate buffered saline) and mixed. The diluted sample was then transported to a sheathed impedance aperture to determine the absolute RBC counts of the sample. At the same time, about 200 microliters of the diluted whole blood sample was transferred into the reticulocyte cup which contains 600 microliters of the reagent of the present invention. This reagent contained of 50 mM imidazole buffer, pH adjusted with 1N HCl to 7.0+0.1, 6.4 g/L of NaCl, 0.2 μg/ml of 2-butyl-4-[2,3-dihydro-3-methyl-(benzo-1,3-thiazol-2-yl)-methylidene]-1-phenylquinolinium iodide, 10 mgs per ml BIGCHAP, 0.03 Proclin® 300. The sample/reagent mixture was then transported to the sheathed optical flow cell for scatter and fluorescence detection. The system detection process has previously been described above, and the entire contents of U.S. patent application Ser. No. 08/283,379, entitled "METHOD AND APPARATUS FOR PERFORMING AUTOMATED ANALYSIS", and filed on Aug. 1, 1994, are herein incorporated by reference. The dwell time for the transportation of the sample/reagent mixture can be as little as ten (10) seconds. The RBC population including reticulocytes is gated on the IAS vs FL1 cytogram (FIG. 4a) and the FL1 histogram of the gated RBC population (FIG. 4b) is used for reticulocyte counts and measurements. The 1× display of the FL1 histogram is scaled to show the RBC population peak and the 5× display shows the reticulocyte population. These results show that it is possible to analyze a sample for reticulocytes while simultaneously determining a CBC analysis, and without the need for additional sample incubation equipment or methods, or off-line sample preparation steps.

EXAMPLE 5

Figure 5A:
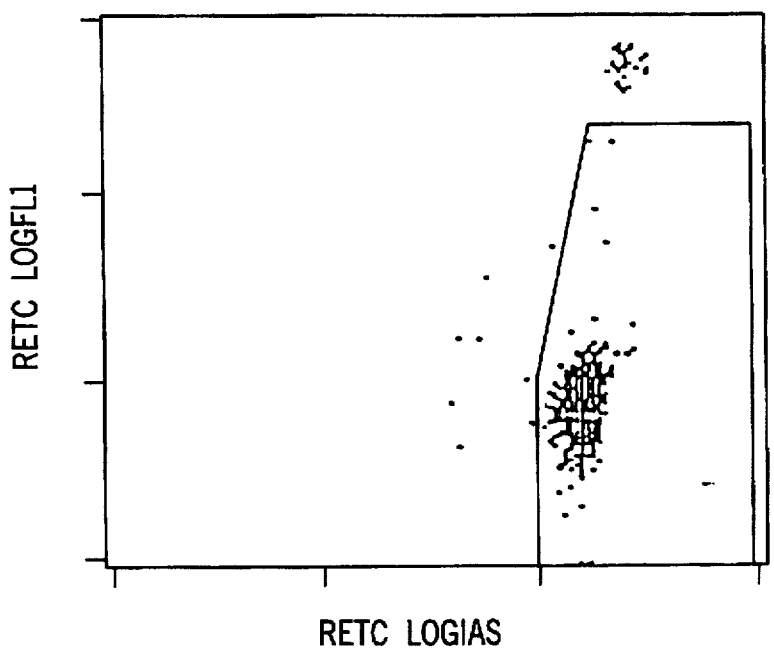
FIG. 5a is an Abbott Laboratories hematology analyzer cytogram of IAS vs FL1 of a clinical blood sample with very low reticulocytes but elevated WBC.
Figure 5B:
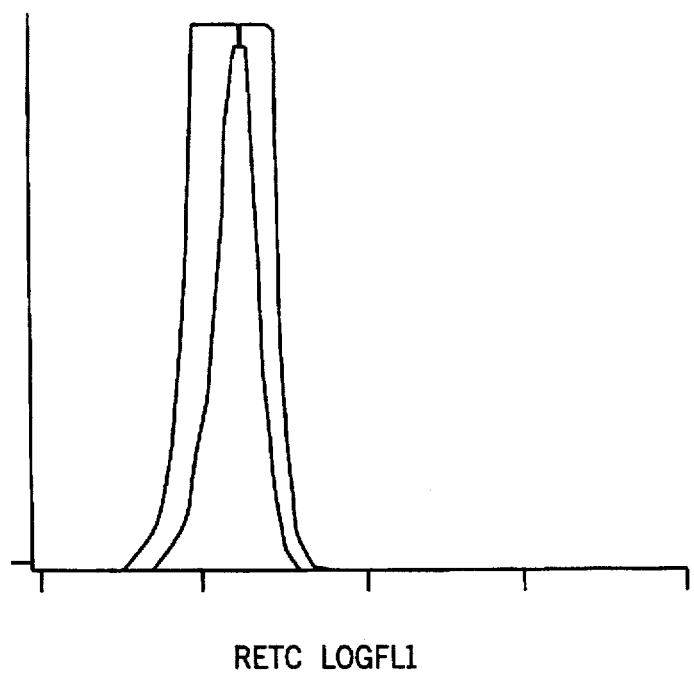
FIG. 5b is a FL1 histogram of the gated RBC and reticulocyte population from FIG. 5a. Both 1× and 5× scale displays of the histogram are shown.

A clinical sample with low concentration of reticulocytes and elevated WBC, as determined by reference methods, is deposited by means of a sample aspiration probe into the RBC cup of the instrument described in U.S. patent application Ser. No. 08/283,379, which contains about 7856 µl of a diluent/sheath solution (an isotonic saline) and mixed. The diluted sample is then transported to the sheathed impedance aperture to determine the absolute RBC counts of the sample. In the interim, about 200 microliters of the diluted sample is transferred into the reticulocyte cup which contains 600 microliters of the reagent of the present invention comprised of 50 him imidazole buffer, pH adjusted with 1N HCl to 7.0+0.1, 6.4 g/L of NaCl, 0.2 micrograms per 1.0 ml of 2-butyl-4-[2,3-dihydro-3-methyl-(benzo-1,3-thiazol-2-yl)-methylidene]-1-phenylquinolinium iodide, 0.2% Pluronic® F127 and 2.5 mg/dl n-Dodecyl-D-Maltoside, 0.03% Proclin® 300 and mixed. The sample/reagent mixture was then transported to the sheathed optical flow cell 100 for detection. The system detection process has already been described above. The RBC population including reticulocytes is gated on the IAS vs FL1 cytogram (FIG. 5a) and the FL1 histogram of the gated RBC population (FIG. 5b) is used for reticulocyte counts and RMI measurements (Retic counts were too low to calculate RMI for this sample). The FIG. 5b FL1 histograms are scaled to show both the RBC population peak (1× display) and the reticulocyte population (5× display). No detectable reticulocyte population is observable in this sample.

EXAMPLE 6

Figure 6A:
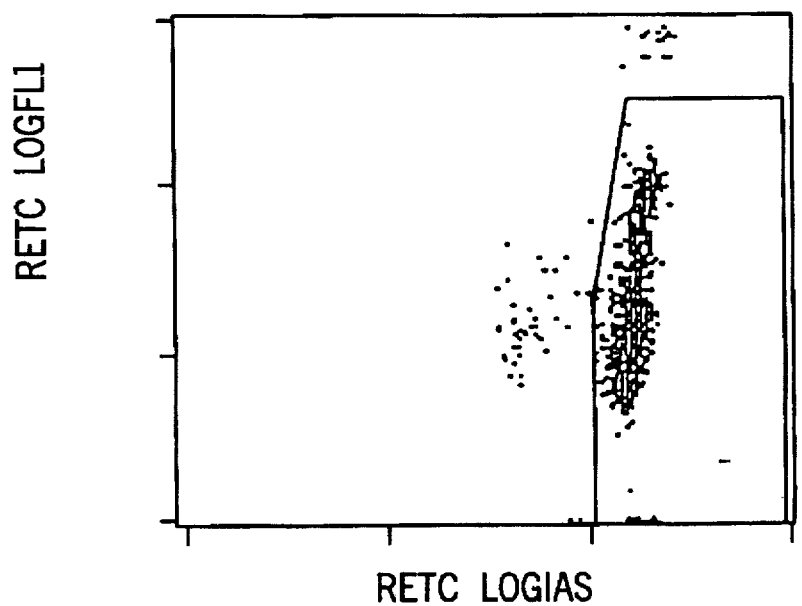
FIG. 6a is an Abbott Laboratories hematology analyzer cytogram of IAS vs FL1 of an anti-coagulated clinical blood sample with elevated reticulocyte (20.5%) and WBC (96.4 k/L) levels.
Figure 6B:
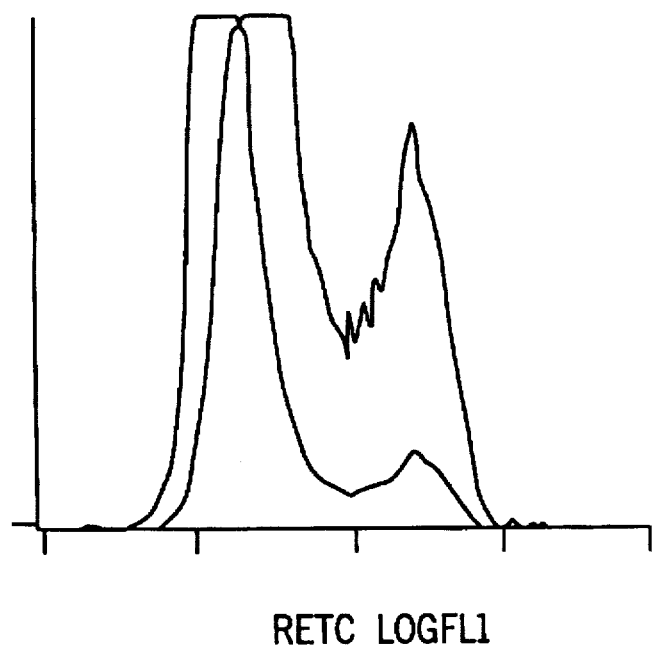
FIG. 6b is a FL1 histogram of the gated RBC and reticulocyte population from FIG. 6a. Both 1× and 5× scale displays of the histogram are shown.

For this example, a clinical sample with elevated reticulocytes (20% as determined by a reference method) and elevated WBC (96 k/L) was used. The sample was processed as described in Example 4. The results are presented in FIGS. 6a and 6b. As the data show, the present invention accurately excludes WBCs and platelets and able to identify and count both dim and bright reticulocytes. The system produced an elevated RMI value of 69.2% on this sample using the algorithm described above.

EXAMPLE 7

Figure 7:
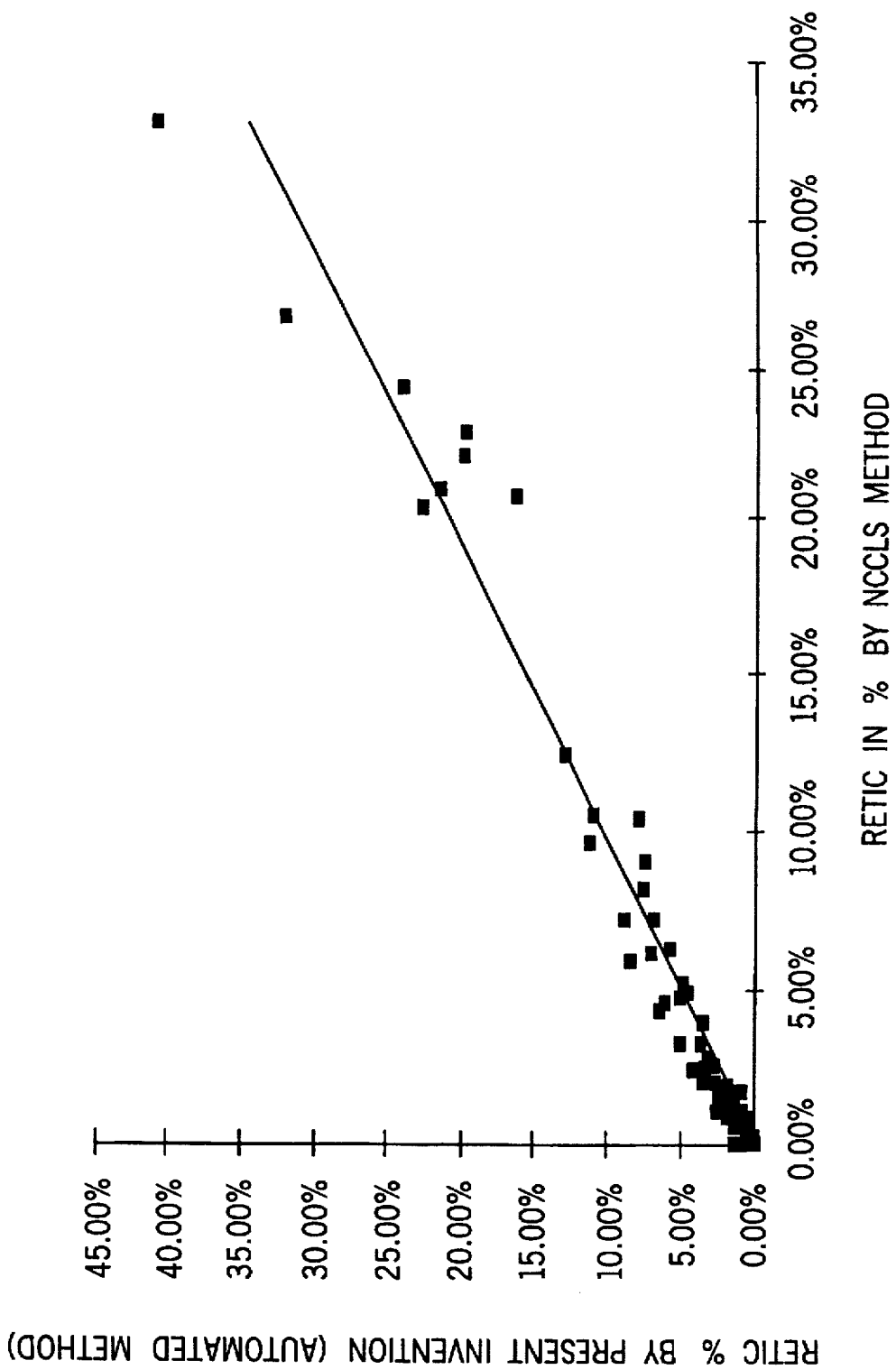
FIG. 7 is a graphical depiction of the comparison of reticulocyte results obtained by practicing the National Committee for Clinical Laboratory Standards ("NCCLS") method vs an automated method of the present invention.
Figure 8:
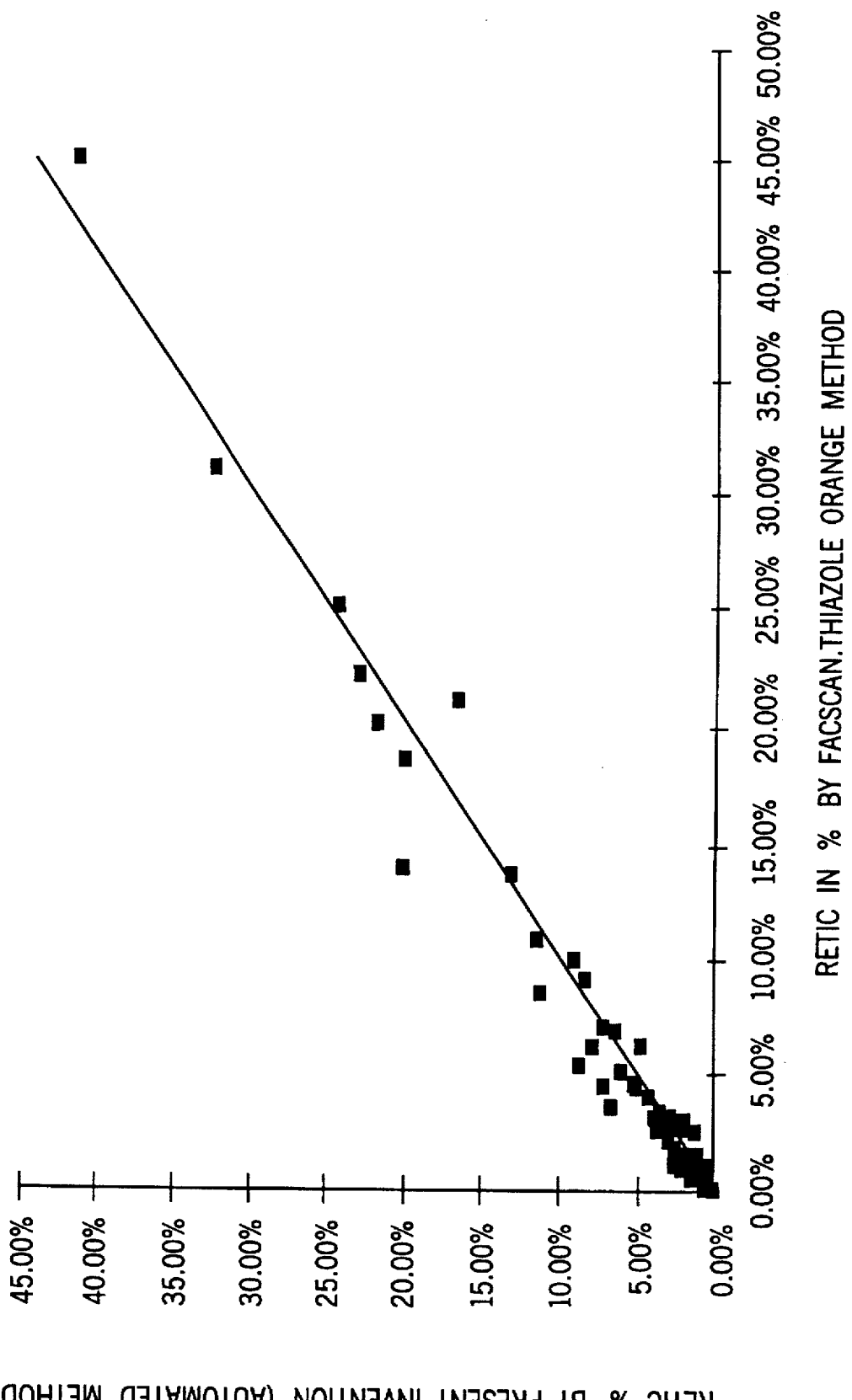
FIG. 8 is a graphical depiction showing a comparison of linear regression data for reticulocyte results obtained by practicing a thiazole orange staining method vs an automated method of the present invention for detecting reticulocytes. The same clinical samples presented in FIG. 7 were used for the analysis.

Seventy seven (77) clinical samples were analyzed on a high throughput multi-parameter hematology analyzer as described in Example 4 and also on a FACScan® flow cytometer as described in Example 1 but using a thiazole orange (TO) method which requires 30 minutes of incubation at room temperature (U.S. Pat. No. 4,883,867). The NCCLS reference method (see section Prior Art for detail) was also performed on each sample. Then the results of the present, no incubation, inventive method were compared to that of the TO and NCCLS methods. The linear regression plots are presented in FIGS. 7 and 8. As the data show, the results of the present invention correlate well with that of both NCCLS microscopic method (R=0.982, slope=1.05, Y-intercept=0.002) and the TO method (R=0.986, slope=0.964, Y-intercept=0.005).

EXAMPLE 8

Two EDTA-anti-coagulated rabbit blood samples were obtained, one from a normal rabbit (sample #1) and another from a rabbit with reticulocytosis (sample #2). Sample µl contained 1.9% reticulocytes and sample #2 contained over 90% reticulocytes. The linearity samples were prepared according to the following protocol:

1. RBC concentration of both samples was adjusted to 3.5+0.05 M/L.

2. Six (6) levels of linearity samples were prepared by mixing the two samples as shown in the Table below:

| Tube No. | Sample #1 | Sample #2 |
| --- | --- | --- |
| 1 | 0.00 ml | 1.50 ml |
| 2 | 0.30 ml | 1.20 ml |
| 3 | 0.60 ml | 0.90 ml |
| 4 | 0.90 ml | 0.60 ml |
| 5 | 1.20 ml | 0.30 ml |
| 6 | 1.35 ml | 0.15 ml |

3. The samples were analyzed on the hematology analyzer of U.S. patent application Ser. No. 08/283,379.

4. The theoretical values for reticulocyte % and absolute count per µl of the whole blood sample were calculated according to the following equation:

Theoretical Retic % of the sample=[(n/1.5)×A%]+[(m/1.5)×B%]×100 where:

n=volume of sample #1 in the linearity sample
m=volume of sample #2 in the linearity sample
1.5=total volume of the linearity sample
A%=Retic % in the undiluted sample #1
B%=Retic % in the undiluted sample #2

Theoretical Retic Absolute#=[(n×A#)+(m×B#)]/1.5× Theoretical Retic % of the sample where:

n=volume of sample #1 in the linearity sample
m=volume of sample #2 in the linearity sample
1.5=total volume of the linearity sample
A#=Retic # in the undiluted sample #1
B#=Retic # in the undiluted sample #2

5. The linearity curve was plotted using the abscissa for the theoretical values and the ordinate for the values obtained from the multi-parameter hematology instrument.

Figure 9:
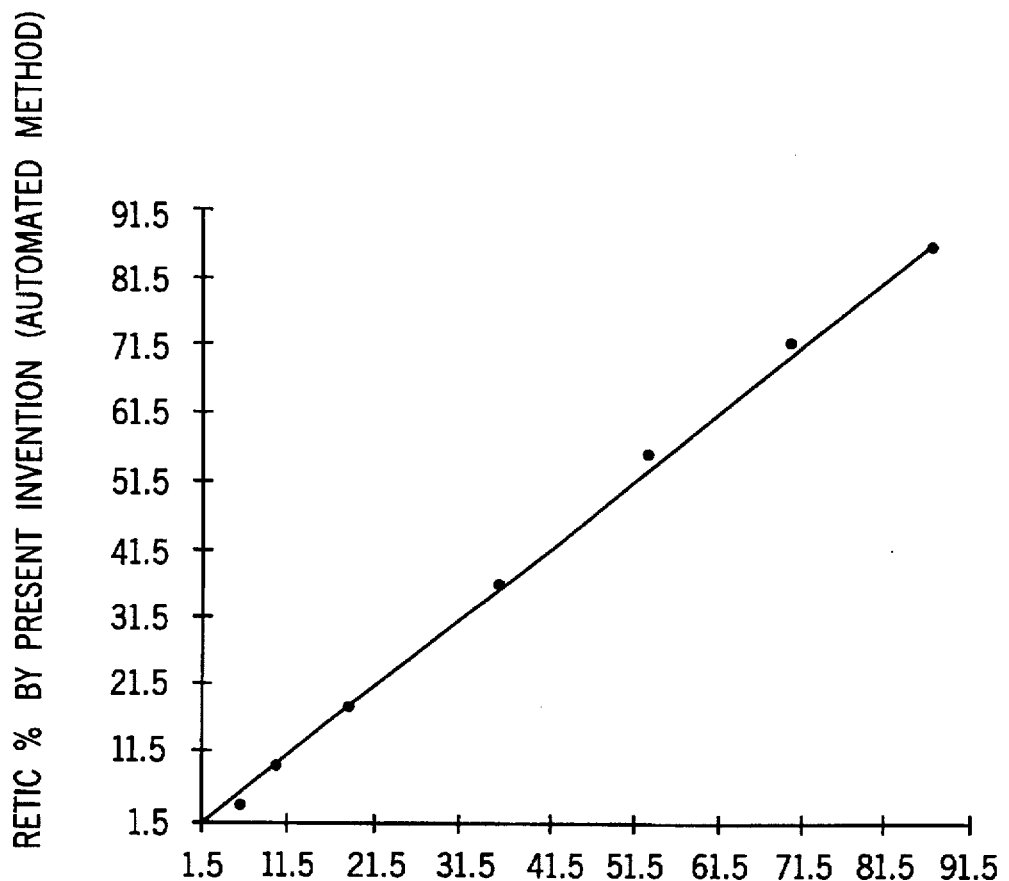
FIG. 9 is a graphical depiction of the linearity of the % reticulocyte measured by practicing an automated method of the present invention.

The results are presented in FIG. 9. As the data show, the method and reagent of the present invention produce a linear response up to reticulocyte concentration of 90%.

EXAMPLE 9

The stability of several reagents prepared according to the present invention, in which various surfactants are evaluated is shown in FIGS. 10–14. This is accomplished by adding RNA to the reagents and scanning the emission spectra of the cyanine nucleic acid stains bound to RNA on a HITACHI F4500® instrument (Excitation 488 nm) according to the following protocol:

1. RNA (Calf Liver RNA, Sigma Cat. No. R7250) solutions (1 mg/ml) were prepared in deionized water.

2. 100 µl of either RNA stock solution was added to 1.6 ml of a test reagent of the present invention and mixed.

3. The emission spectrum of the cyanine nucleic acid stain bound to RNA was then scanned from 450 nm to 650 nm on an HITACHI F4500® instrument (Excitation 488 nm). The full scale for RNA-bound cyanine dye is set at 2,000 for all test reagents.

EXAMPLE 10

Figure 10:
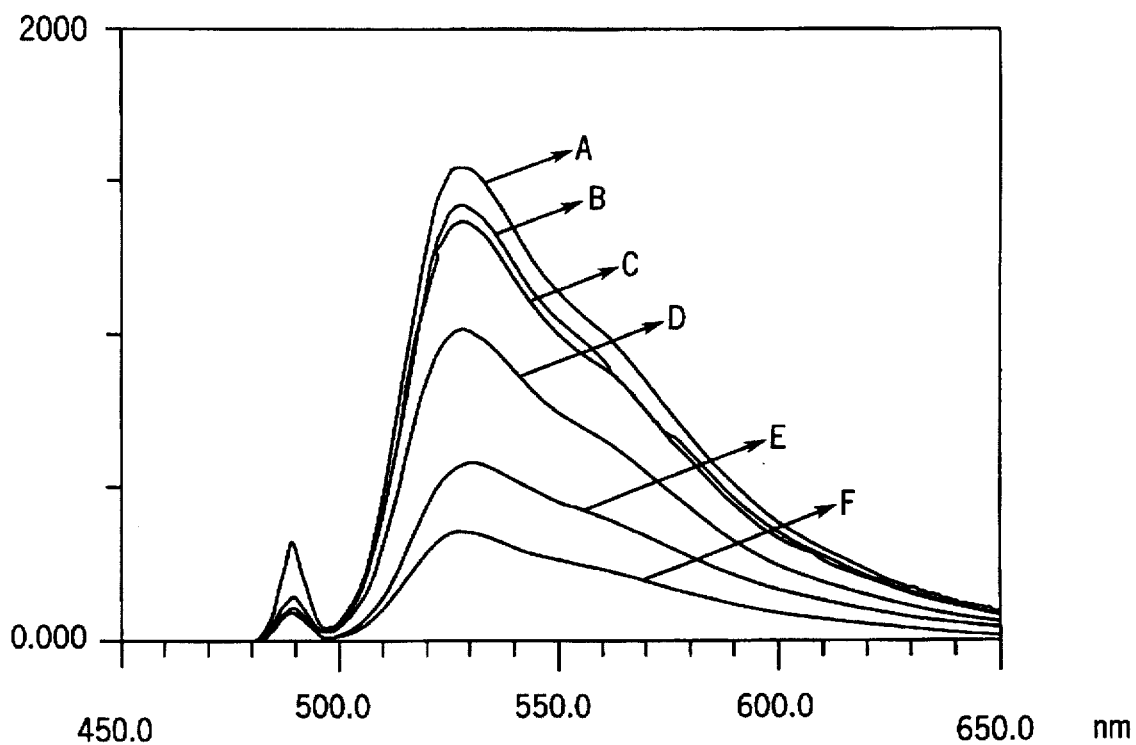
FIG. 10 is a shelf-life study emission spectra of the RNA bound proprietary cyanine dye, 2-butyl-4-[2,3-dihydro-3-methyl-(benzo-1,3-thiazol-2-yl)-methylidene]-1-phenylquinolinium iodide (Molecular Probes, Eugene, Ore.), in the presence and absence of various non-ionic surfactants. The reagents were kept at ambient temperature for three and one-half months.

FIG. 10 is the emission spectra of the RNA bound Sybr 11 dye (Molecular Probes, Inc., Eugene, Ore.) in 50 mM imidazole buffer prepared as described in Example 4 except that 5 different surfactants were evaluated for their effectiveness in stabilizing the cyanine dye, 2-butyl-4-[2,3-dihydro-3-methyl-(benzo-1,3-thiazol-2-yl)-methylidene]-1-phenylquinolinium iodide, in an aqueous solution. All reagents were stored at room temperature for a period of 3.5 months. Starting from the highest peak:

A=BIGCHAP (10 mg %);

B=Maltoside (5 mg %);
C=Pluronic® F127 (0.2%);
D=Cholic Acid, Na Salt (10 mg %);
E=No surfactant added;
F=Caprilic Acid, Na Salt (10 mg %).

As the data show, BIGCHAP, Maltoside and Pluronic® F127 are very effective in keeping the dye in an aqueous buffered solution while Cholic Acid, Na salt and Caprilic Acid, Na Salt were not. As a matter of fact, adding Caprilic Acid to the reagent shortened the shelf-life of the dye.

EXAMPLE 11

Figure 11:
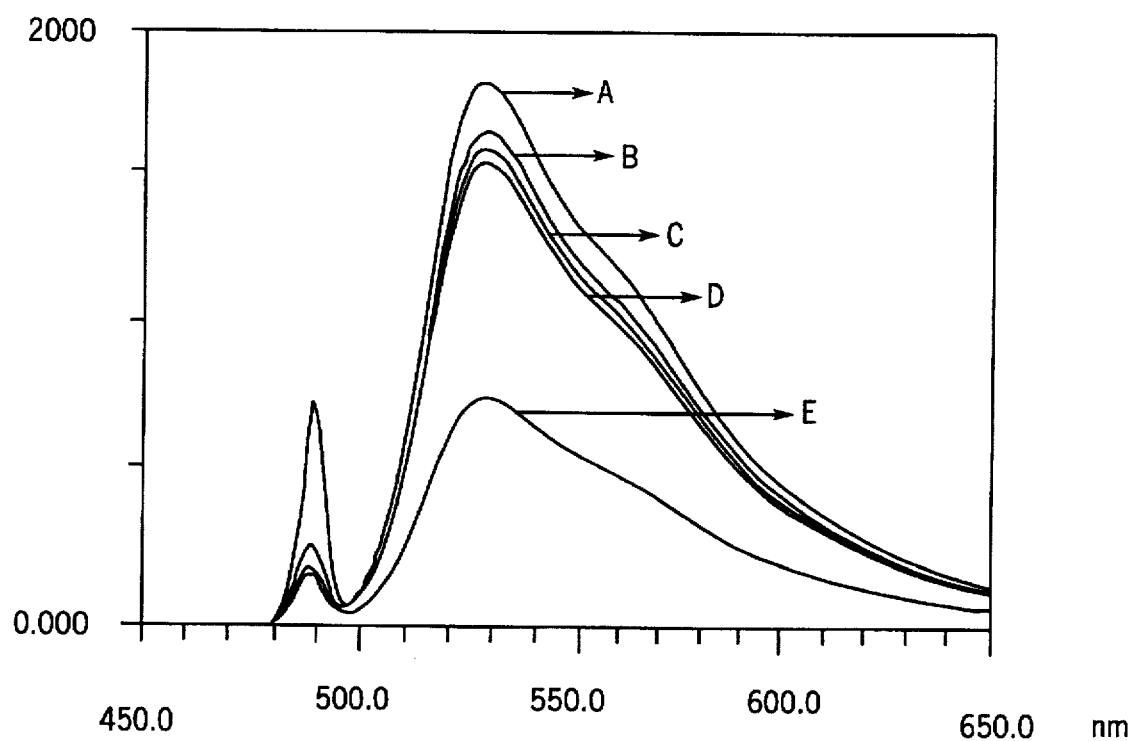
FIG. 11 is a shelf-life study emission spectra of the RNA bound cyanine proprietary dye, 2-butyl-4-[2,3-dihydro-3-methyl-(benzo-1,3-thiazol-2-yl)-methylidene]-1-phenylquinolinium iodide, demonstrating four month stability under refrigeration.

FIG. 11 is the emission spectra of the RNA bound cyanine dye, 2-butyl-4-[2,3-dihydro-3-methyl-(benzo-1,3-thiazol-2-yl)-methylidene]-1-phenylquinolinium iodide, prepared as described in Example 4 with BIGCHAP or Pluronic® F127 surfactants and stored at 4° C. for 4 months. Starting from the highest peak:

A=Freshly prepared control reagent;
B=BIGCHAP (10 mg %);
C=Pluronic® F127 (0.2%);
D=Pluronic® F127 (1.0%);
E=no surfactant.

As can be seen in the figure, there is no significant deterioration of the dye in the present invention during the 4 months test period.

EXAMPLE 12

Figure 12:
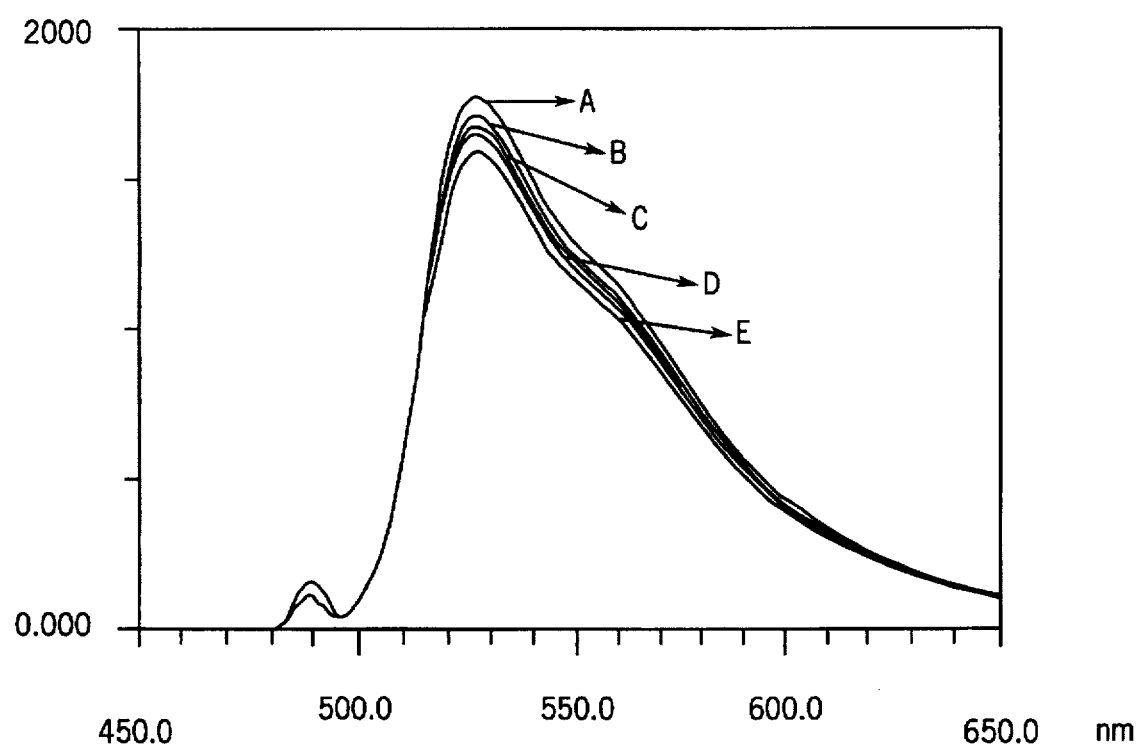
FIG. 12 is a shelf-life study emission spectra of the RNA bound proprietary cyanine dye, 2-butyl-4-[2,3-dihydro-3-methyl-(benzo-1,3-thiazol-2-yl)-methylidene]-1-phenylquinolinium iodide, demonstrating a three week elevated temperature stability.

FIG. 12 is the emission spectra of the RNA bound cyanine dye, 2-butyl-4-[2,3-dihydro-3-methyl-(benzo-1,3-thiazol-2-yl)-methylidene]1-phenylquinolinium iodide, demonstrating a three (3) week elevated temperature stability in the reagent of present invention with 5 mgs % BIGCHAP. The test reagents were prepared as described in Example 4 and RNA addition was prepared according to Example 9 protocol. Starting from the highest peak:

A=4° C.;
B=250° C.;
C=37° C.;
D=450° C.

As the data demonstrates, the addition of the nonionic surfactant, BIGCHAP, to an appropriate aqueous buffered solution makes the cyanine dye less sensitive to elevated temperatures, and therefore, more stable.

EXAMPLE 13

Figure 13:
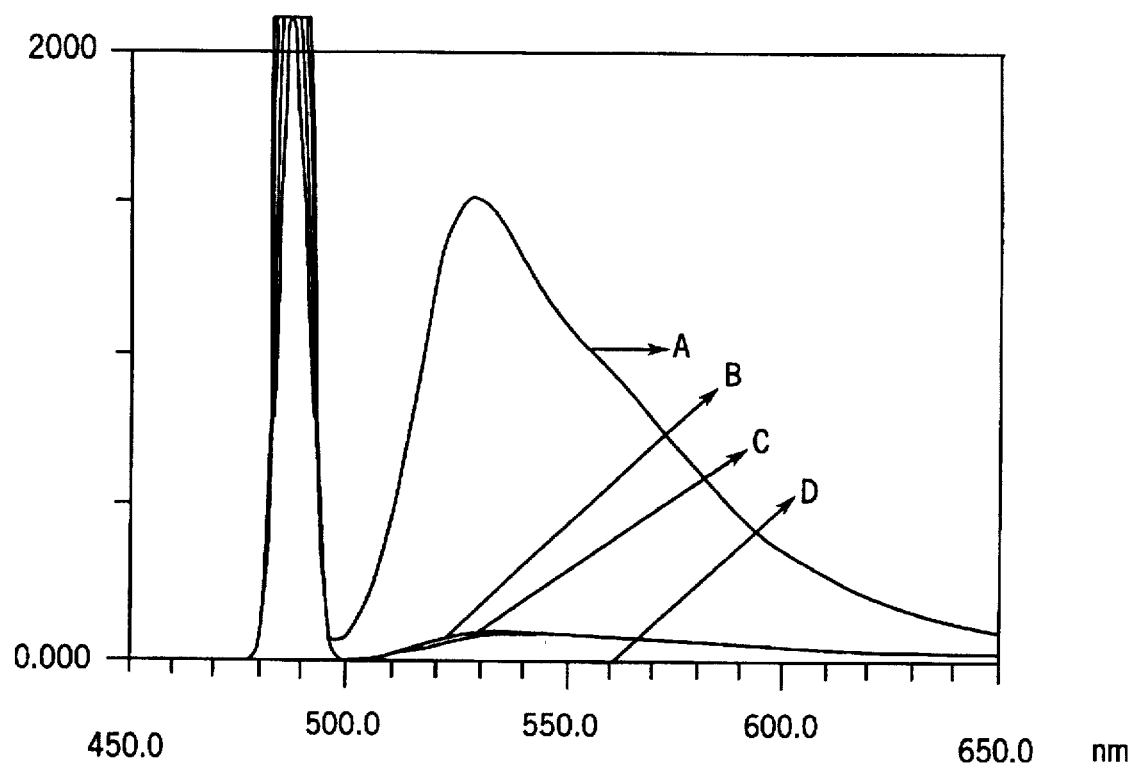
FIG. 13 is a time-study emission spectra of the RNA bound proprietary cyanine dye, 2-methylthio-4-[2,3-dihydro-3-methyl-(benzo-1,3-thiazol-2-yl)-methylidene]-1-phenylquinolinium iodide (Molecular Probes, Eugene, Ore.), in Bis-Tris buffer with and without 1.0% Polyoxypropylene-polyoxyethylene block copolymer ("Pluronic® F127") and stored at ambient temperature for six and one-half months.

FIG. 13 is the emission spectra of the RNA bound 2-methylthio-4-[2,3-dihydro-3-methyl-(benzo-1,3-thiazol-2-yl)-methylidene]-1-phenylquinolinium iodide in Bis-Tris buffer with and without 1.0% Pluronic® F127. The reagents were prepared as described in Example 4 except that Imidazole buffer was replaced with Bis-Tris buffer and 2-butyl-4-[2,3-dihydro-3-methyl-(benzo-1,3-thiazol-2-yl)-methylidene]-1-phenylquinolinium iodide was replaced with 2-methylthio-4-[2,3-dihydro-3-methyl-(benzo-1,3-thiazol-2-yl)-methylidene]-1-phenylquinolinium iodide dye (Molecular Probes, Inc., Eugene, Ore.) and stored at ambient temperature for 6.5 months.

Starting from the highest peak:

A=2-methylthio-4-[2,3-dihydro-3-methyl-(benzo-1,3-thiazol-2-yl)-methylidene]-1-phenylquinolinium iodide reagent with 1.0% Pluronic® F127;
B=2-methylthio-4-[2,3-dihydro-3-methyl-(benzo-1,3-thiazol-2-yl)-methylidene]-1-phenylquinolinium iodide in Bis-Tris buffer without any surfactant;
C=2-methylthio-4-[2,3-dihydro-3-methyl-(benzo-1,3-thiazol-2-yl)-methylidene]-1-phenylquinolinium iodide in Imidazole buffer without any surfactant;
D=2-methylthio-4-[2,3-dihydro-3-methyl-(benzo-1,3-thiazol-2-yl)-methylidene]-1-phenylquinolinium iodide in Glycyl-glycine buffer with 1.0% Pluronic® F127.

The results demonstrate that the stabilization of this cyanine dye requires an appropriate combination of a buffer and a surfactant.

EXAMPLE 14

Figure 14:
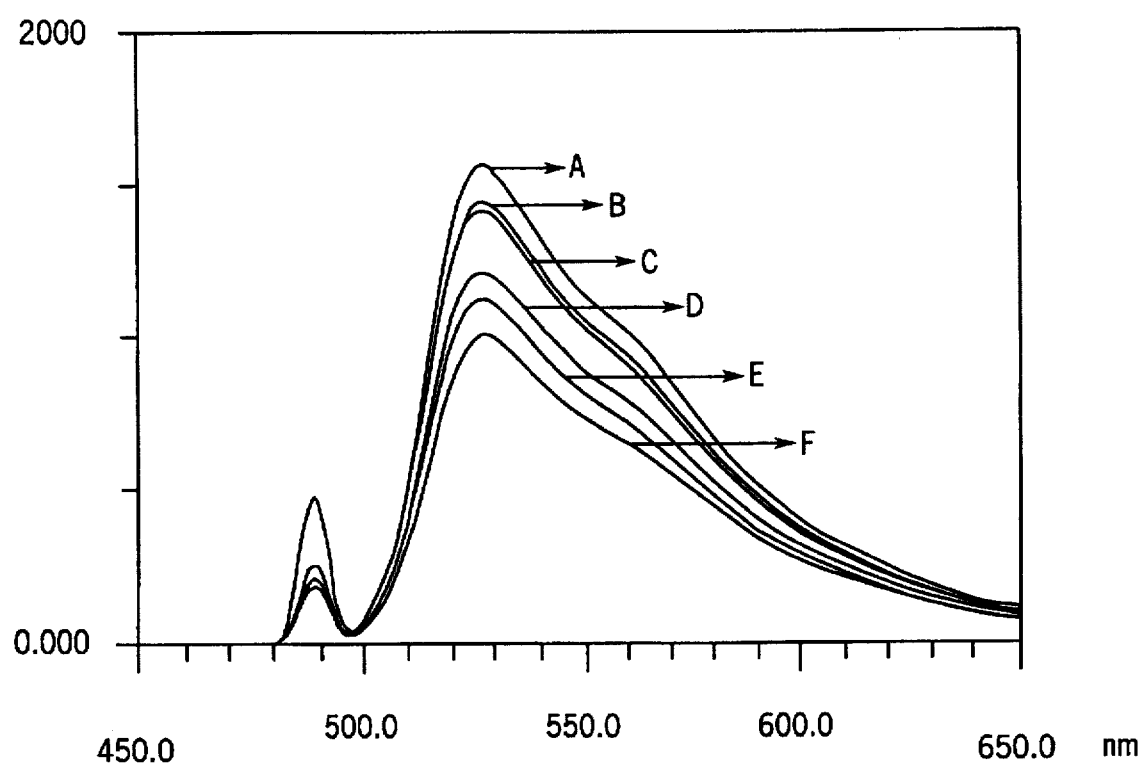
FIG. 14 is a shelf-life study emission spectra of the RNA bound proprietary cyanine dye, 2-butyl-4-[2,3-dihydro-3-methyl-(benzo-1,3-thiazol-2-yl)-methylidene]-1-phenylquinolinium iodide, in different buffers with 0.2% Pluronic® F127. All reagents were stored at room temperature for six weeks.

FIG. 14 is the emission spectra of the RNA bound 2-butyl-4-[2,3-dihydro-3-methyl-(benzo-1,3-thiazol-2-yl)-methylidene]-1-phenylquinolinium iodide cyanine dye in different buffers along with 0.2% Pluronic® F127. All reagents were stored at room temperature for six weeks.

Starting from the highest peak:

A=Tris buffer;
B=Bis-Tris buffer;
C=Imidazole;
D=Hepes buffer;
E=Glycyl-glycine buffer;
F=Phosphate buffer.

As this data show, Tris, Bis-Tris and Imidazole buffers preserve the dye well while Glycyl-glycine and Phosphate buffers do not.

EXAMPLE 15

Figure 15A:
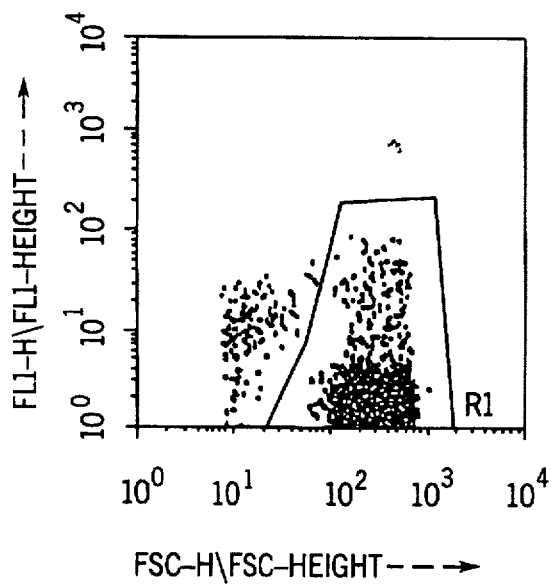
FIG. 15a is a FACScan® cytometer two dimensional display of FSC vs FL1 signals.
Figure 15B:
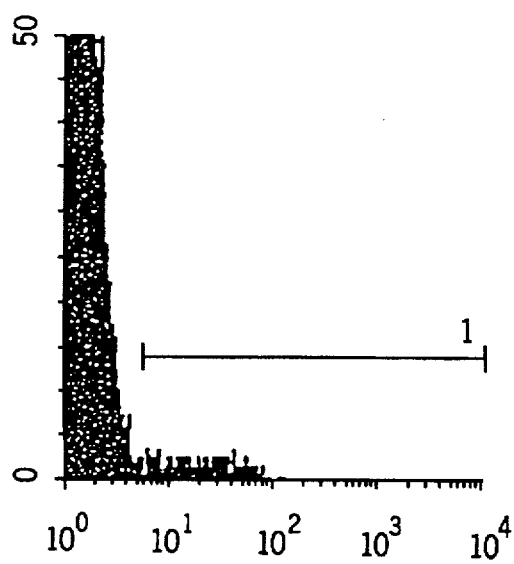
Figure 15C:
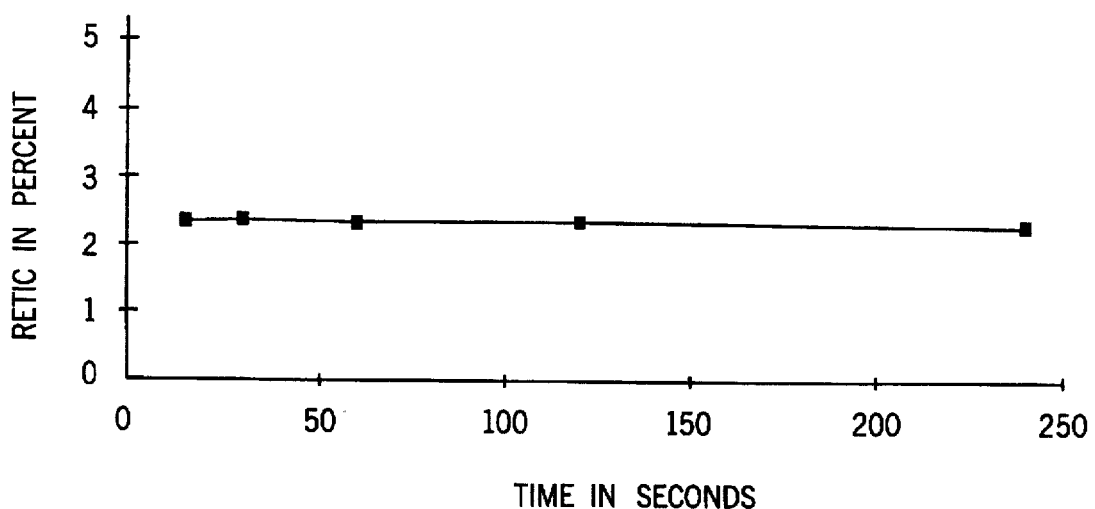
FIG. 15c is a time study performed on the FACScan® flow cytometer expressed as reticulocyte % from 15 seconds up to 4.0 minutes.

Five (5) microliters of a normal sample with about 2.3% reticulocytes were mixed with 1.0 ml of the reagent of the present invention comprised of 50 mM Tris buffer, pH adjusted with 1N HCl to 7.0+0.1, osmolarity adjusted to 290 mOsm/L with NaCl, 0.2 μg/ml of 4-[2,3-dihydro-3-methyl-(benzo-1,3-thiazol-2-yl)-methylidene]-1-phenylquinolinium tosylate (Molecular Probes, Inc., Eugene, Ore.), 0.2% Pluronic® F127, and 0.03% Proclin® 300. The sample/reagent mixtures were then run on a FACScan® flow cytometer within 15 seconds to determine the % of reticulocytes in the samples. FIG. 15a shows the FACScan® cytometer two dimensional display of FSC vs FL1 signals; and FIG. 15b shows the FL1 histogram of the gated red cell population. FIG. 15c is a time study performed on the FACScan® flow cytometer expressed as reticulocyte % from 15 seconds up to 4.0 minutes. As can be seen in the Figures the RBC+ reticulocyte gate cleanly separates reticulocytes from platelets and WBCs and the reticulocyte staining is so rapid that the % reticulocyte reaches the steady state within 15 seconds. Such rapid staining enables the incorporation of the detection onto automated hematology analyzers, as well as flow cytometers.

We claim:

1. An aqueous, nucleic acid staining reagent comprising: a reticulocyte staining amount of an unsymmetrical cyanine dye; from about 20 mM to about 60 mM of a buffer solution, selected from the group consisting of imidazole, Hepes, Bis-Tris and Tris buffers; and a dye stabilizing amount of a non-ionic surfactant selected from the group consisting of N,N-bis[3-D-Glucon-amidopropyl]cholamide, n-Dodecyl-D-Maltoside, a polyoxypropylene-polyoxyethylene block copolymer, n-Tetradecyl-D-Maltoside, Decanoyl-N-methylglucamide, n-Dodecyl-D-glucopyranoside and n-Decyl-D-glucopyranoside, wherein said reagent has a pH from about 6.0 to about 8.0 and an osmolarity adjusted to about 230 to about 340 mOsm/l with a mono-, or di-, valent alkali salt which do not interfere with the cyanine dye or precipitate in the aqueous reagent solution.

2. The reagent of claim 1 wherein the unsymmetrical cyanine dye is cyclic substituted.

3. The reagent of claim 1 wherein said unsymmetrical cyanine dye is selected from the group consisting of 2-butyl-4-(2,3-dihydro-3-methyl-(benzo-1,3-thiazol-2-yl)-methylidene)-1-phenylquinolinium iodide, 2-diethylamino-4-(2,3-dihydro-3-methyl-(benzo-1,3-thiazol-2-yl)-methylidene)-1-phenylquinolinium iodide, 2-methylthio-4-(2,3-dihydro-3-methyl-(benzo-1,3-thiazol-2-yl)-methylidene)-1-phenylquinolinium iodide, and 4-(2,3-dihydro-3-methyl-(benzo-1,3-thiazol-2-yl)-methylidene)-1-phenylquinolinium tosylate.

4. The reagent of claim 1 wherein said unsymmetrical cyanine dye is 2-butyl-4-(2,3-dihydro-3-methyl-(benzo-1,3-thiazol-2-yl)-methylidene)-1-phenylquinolinium iodide.

5. The reagent of claim 3 wherein the reticulocyte staining amount of the unsymmetrical cyanine dye is from about 0.1 µg/ml to about 0.3 µg/ml.

6. The reagent of claim 5 wherein the buffer is imidazole.

7. The reagent of claim 5 wherein the non-ionic surfactant is present in an amount from about 0.1 g/dl to about 1.0 g/dl.

8. The reagent of claim 7 wherein the non-ionic surfactant is a polyoxypropylene-polyoxyethylene block copolymer.

9. The reagent of claim 5 wherein the non-ionic surfactant is present in an amount from about 5 mg/dl to about 20 mg/dl.

10. The reagent of claim 9 wherein the non-ionic surfactant is N,N-bis[3-D-Glucon-amidopropyl]cholamide.

11. The reagent of claim 1 further comprising an effective amount of microbial growth inhibiting preservative.

12. The reagent of claim 11 wherein the preservative is selected from the group consisting of (5-chloro-2-methyl-4-isothiazolin-3-one (2.0%–2.5%) and 2-methyl-4-isothiazolin-3-one (0.7%–0.9%)), (5-chloro-2-methyl-4-isothiazolin-3-one (1.05%–1.25%) and 2-methyl-4-isothiazolin-3-one (0.25%–0.45%)), and sodium azide.

13. An aqueous, nucleic acid staining reagent comprising:

from about 0.1 µg/ml to about 0.3 µg/ml of a dye selected from the group consisting of 2-butyl-4-(2,3-dihydro-3-methyl-(benzo-1,3-thiazol-2-yl)-methylidene)-1-phenylquinolinium iodide, 2-diethylamino-4-(2,3-dihydro-3-methyl-(benzo-1,3-thiazol-2-yl)-methylidene)-1-phenylquinolinium iodide, and 2-methylthio-4-(2,3-dihydro-3-methyl-(benzo-1,3-thiazol-2-yl)-methylidene)-1-phenylquinolinium iodide;

from about 40 mM to about 60 mM of a buffer selected from the group consisting of imidazole, Tris and Bis-Tris buffer; and a dye stabilizing amount of a non-ionic surfactant selected from the group consisting of N,N-bischolamide and a polyoxypropylene-polyoxyethylene block copolymer, wherein said reagent has a pH from about 6.8 to about 7.2 and an osmolarity adjusted to about 280 to about 310 mOsm/l with a mono-, or di-, valent alkali salt selected from the group consisting of NaCl, KCl, LiCl, $CaCl_2$, $MgCl_2$ and $ZnCl_2$.

14. The reagent of claim 13 wherein the non-ionic surfactant is from about 5 mg/dl to about 20 mg/dl of N,N-bis (3-D-Glucon-amidopropyl)cholamide.

15. The reagent of claim 13 wherein the non-ionic surfactant is from about 0.1 g/dl to about 1.0 g/dl of a polyoxypropylene-polyoxyethylene block copolymer.

* * * * *